(12) United States Patent
Ueno et al.

(10) Patent No.: US 7,643,140 B2
(45) Date of Patent: Jan. 5, 2010

(54) METHOD AND APPARATUS FOR INSPECTING A SEMICONDUCTOR DEVICE

(75) Inventors: Taketo Ueno, Kawasaki (JP); Yasuhiro Yoshitake, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 6 days.

(21) Appl. No.: 12/046,521

(22) Filed: Mar. 12, 2008

(65) Prior Publication Data
US 2008/0239289 A1 Oct. 2, 2008

(30) Foreign Application Priority Data
Mar. 29, 2007 (JP) ............................. 2007-088744

(51) Int. Cl.
| | |
|---|---|
| G01N 21/00 | (2006.01) |
| G01N 21/88 | (2006.01) |
| G06K 9/00 | (2006.01) |
| G06K 9/32 | (2006.01) |

(52) U.S. Cl. .............. 356/237.4; 356/237.5; 356/237.2; 382/141; 382/145; 382/249

(58) Field of Classification Search ... 356/237.1–237.6; 382/141, 144, 145, 149, 151, 154, 249; 250/372
See application file for complete search history.

(56) References Cited

U.S. PATENT DOCUMENTS

| | | | | |
|---|---|---|---|---|
| 6,281,024 B1 * | 8/2001 | Yoshitake et al. | .............. | 438/8 |
| 6,452,677 B1 * | 9/2002 | Do et al. | ...................... | 356/394 |
| 7,020,350 B2 * | 3/2006 | Sakai et al. | .................. | 382/294 |
| 7,127,126 B2 * | 10/2006 | Sakai et al. | .................. | 382/294 |
| 7,369,223 B2 * | 5/2008 | Hamamatsu et al. | ...... | 356/237.2 |
| 2006/0002604 A1 * | 1/2006 | Sakai et al. | .................. | 382/141 |
| 2007/0121106 A1 * | 5/2007 | Shibata et al. | ............ | 356/237.2 |

FOREIGN PATENT DOCUMENTS

| | | | |
|---|---|---|---|
| JP | 61151410 A | * | 7/1986 |
| JP | 2003-83907 | | 3/2003 |
| JP | 2003-98113 | | 4/2003 |
| JP | 2003-271927 | | 9/2003 |

* cited by examiner

*Primary Examiner*—Sang Nguyen
(74) *Attorney, Agent, or Firm*—Antonelli, Terry, Stout & Kraus, LLP.

(57) ABSTRACT

A semiconductor defect inspection apparatus using a method of comparing an inspected image with a reference image includes the following: (1) a light source and an illuminating optical system, (2) plural defect optical imaging systems and photo detectors for scattered light detection, (3) a substrate holder and a stage for a scan, (4) means for obtaining the misalignment information on an adjacent die image using the inspection image of a defect optical imaging system with the highest spatial resolution, and means for transmitting the misalignment information to all the defect inspection image processing units, (5) means for correcting misalignment information so that a design and adjustment condition of each optical imaging system may be suited, and means for calculating a difference image between dies based on the corrected misalignment information, and (6) a defect detection and image processing unit for performing defect determination and detection processing based on the difference image between the dies.

14 Claims, 27 Drawing Sheets

IMAGE OF
OPTICAL SYSTEM 1

IMAGE COORDINATES
OF DEFECT        (x1,y1)

IMAGE OF
OPTICAL SYSTEM 2

(x2,y2)

FOCUS STATE

DEFOCUS STATE (a)

(b)

METHOD AND APPARATUS FOR INSPECTING A SEMICONDUCTOR DEVICE

BACKGROUND OF THE INVENTION

The present invention relates to a method and apparatus for defect inspection to detect a small pattern defect, a foreign substance, etc. from the difference between the images of an inspected object using light and a reference, and especially to a method and apparatus for inspecting optically the defect of a semiconductor device, a photo mask, a liquid crystal, etc.

In manufacturing of a semiconductor device, a substrate (wafer) is processed by hundreds of manufacturing processes, and a semiconductor device is formed therewith. In each process, a foreign substance may adhere on the substrate (wafer) or a pattern defect may be produced by variation in manufacturing process, which are causes for producing a semiconductor device with inferior characteristics. In the defect inspection system of a semiconductor device, the needs for a classification are growing of various kinds of DOI (Defect Of Interest) and defection of a defect not to be wanted to detect, as well as detection of smaller defects or foreign substances with progress of fine pattern forming process. In order to meet such needs, plural defect inspection apparatuses equipped with optical imaging systems and image processing systems (hereafter called a probe head) are developed, manufactured and on the market in recent years, aiming at the increase in detectable kinds of defect and the improvement in defect detecting performance by using the detection signal in each optical imaging system. These defect inspection apparatuses are actually used in the semiconductor production line.

After the completion of processes such as a lithography, a film forming process, and an etching process, etc. the defect inspection apparatus for a semiconductor device inspects the substrate surface to defect or a foreign substance generated in the processes, and issues an instruction to clean the apparatus used in the process and prevents inferior goods to be otherwise generated by delivering a substrate with a fatal defect to the following process by detecting a defect at an early stage.

In the middle of formation process of a semiconductor device with a substrate, the substrate is loaded to the defect inspection apparatus. The surface of the substrate (wafer) is imaged in the middle of formation of a semiconductor device, and based on the images thus obtained, a defect determination processing is performed by utilizing a defect signal decision threshold disclosed in JP-A-2003-83907, 2003-98113, and 2003-271927, etc., a defect determination is made and the number defects etc. on the substrate are outputted.

When the number defects Nt detected is less than the threshold Nc of defect set up beforehand, the substrate is send to the next process as it is. When the detected defective number Nt is large, the propriety of the substrate reproduction is decided after issuing the cleaning implementation instruction to a previous process device. When the substrate is decided to be refreshable, after washing the substrate in a washing process, this inspection process is applied again, and then sent to the next process.

The substrate (wafer) in the middle of formation of a semiconductor device is an inspected object having the same pattern of portions 1 and 1' regularly in a line as shown in FIG. 4 (hereafter called a die). The defect inspection method and defect inspection apparatus of the present invention is to compare the images of adjacent dies at the same position in the corresponding coordinates in the dies, respectively, and decide a defective detection based on the differences between the two.

However, if a whole scanning system vibrates or inclines when a stage scanning, a gap will arise in the image formation position of a optical imaging system, making unable to obtain the signals from the same corresponding part of dies for every die opening. This is the major cause of a misalignment of the images between adjacent dies.

An inspection apparatus with plural probe heads is proposed and developed in recent years, and has been applied to a semiconductor production line.

In an optical inspection apparatus with such plural probe heads, a probe head must be installed so that the heads may not interfere with one another. For this reason a case arises where it is difficult to give object lenses the same numerical aperture and some object lenses have to be designed to have smaller apertures, resulting in lower optical resolving power with the system. Accordingly, misalignment calculation accuracy falls when carrying out image misalignment calculation between reference image and inspection image as the preceding step of calculating the difference image between dies. And falling down of the misalignment calculation accuracy causes a decrease in the calculation accuracy of a difference image, and resulting in deterioration of the defect detecting performance.

SUMMARY OF THE INVENTION

In optical inspection apparatuses having plural probe heads with different sensitivity, the present invention provides a method and apparatus for inspecting a fatal defect of smaller particles or pattern defects with higher detection sensitivity concerning the optical defect inspection method and apparatus for a semiconductor device using a method of comparing an inspected image with a reference image. In addition, the difference of the images resulting from scanning is made small by acquiring two or more die images at the same positions through one x direction stage scan.

That is, in order to accomplish an above mentioned subject, the inspection apparatus of the present invention is configured as a system including the following means so as to improve detection sensitivity:

(1): a light source and a illumination-light optical system such as a laser, (2): plural defect optical imaging systems and photo detectors for detecting scattered light, (3): a substrate holder and a stage for a scan, (4): means for obtaining the misalignment information from the adjacent die image using the inspection image of a defect optical imaging system with the highest spatial resolution, and means for transmitting the misalignment information to all the defective inspection image processing units, (5): means for correcting the misalignment information acquired in (3) to match a design and adjustment condition of each optical imaging system, and means for calculating the difference image between dies based on the corrected misalignment information, (6): a defective inspection image processing unit for performing a defect determination/detection processing based on the difference image between dies obtained in (5), (7): means for calculating and setting up the design and adjustment conditions manually or semiautomatic of each optical imaging system to be used for the correction means of (5).

The present invention is characterized mainly in that above described in (4), (5), and (7).

According to the present invention, calculating misalignment information using a high resolution inspection image, and applying this information also to the inspection image of low resolution the difference image between adjacent dies is obtained, and a defect determination and inspection processing are performed. Also in the optical imaging system of comparatively low resolution, the defect inspection method with higher detection sensitivity can be provided. The image misalignment calculating unit between adjacent dies with many calculative complexities is installed in the image processing unit and the number of units is reduced, so that a method is provided the whole image processing unit can be miniaturized requiring a small footprint.

These and other objects, features and advantages of the invention will be apparent from the following more particular description of preferred embodiments of the invention, as illustrated in the accompanying drawings.

DETAILED DESCRIPTION OF THE PREFERRED EMBODIMENTS

A first embodiment of the present invention is first described with reference to the accompanied drawings.

First Embodiment

The first embodiment is described in the following using FIGS. 1 to 8.

Figure 1:
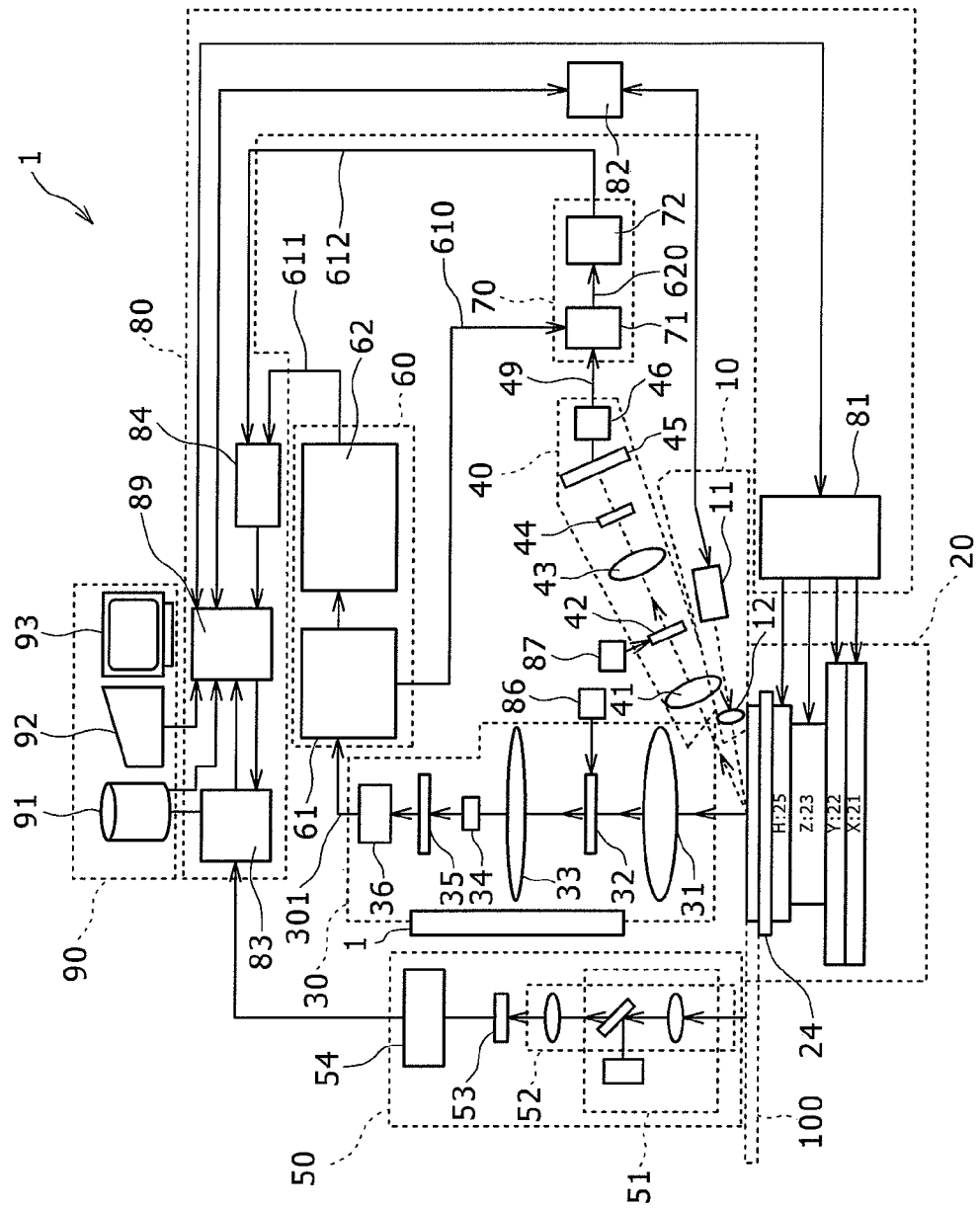
FIG. 1 is a drawing for explaining the block diagram of the substrate inspection apparatus in accordance with an embodiment of the present invention.

The block diagram of an inspection apparatus 1 is shown in FIG. 1. The inspection apparatus 1 is constituted of an illuminating optical system 10, a substrate scanning system 20, a first optical imaging system 30, a second optical imaging system 40, focus measurement system 50, a first image processing system 60, a second image processing system 70, a control processing system 80, and an interface system 90.

The illuminating optical system 10 includes a laser light source 1, and a lens 12 for beam shaping, and the light emitted from the laser light source 11 is suitably shaped and illuminates an inspected substrate 100. The substrate scanning system 20 includes an X stage 21, a Y stage 22, a Z stage 23, a substrate chuck 24, and a θ stage 25.

The first optical imaging system 30 includes an object lens 31, a spatial filter 32, an image formation lens 33, a polarizing filter 34, a photo sensor 35, and an A/D-conversion unit 36.

The second optical imaging system 40 includes an object lens 41, a spatial filter 42, an image formation lens 43, a polarizing filter 44, a photo sensor 45, and an A/D-conversion unit 46.

The focus measurement system 50 includes an illuminating optical system 51, a optical imaging system 52, a photo sensor 53, and defocus distance calculation processing unit 54.

The first image processing system 60 includes an image misalignment information calculation unit 61 between adjacent dies, and a data processing unit 62 for performing defect determination and detection processing using the difference image between dies.

The second image processing system 70 includes a misalignment information correction unit 71 for correcting the above-mentioned combined image misalignment information, and a data processing unit 72 for performing defect determination and detection processing using the difference image between dies.

The control and processing system 80 includes a transfer system control unit 81 for controlling at least transfer system 20, an illumination light source control unit 82, a sensor control unit 83 for obtaining an image by synchronizing the first optical imaging system 30 with the second optical imaging system 40, a defect information processing unit 84 for merging processing and sorting processing of defect information 600 outputted from the first image processing system 60 and the second image processing system 70, and control unit 89 for controlling the whole units.

The interface system 90 includes a data accumulating section 91 for accumulating defect information 650 processed and outputted at least from the control and processing unit 80, an input section 92 for setting up inspection conditions and inputting control processing information, and a display section 93 for displaying defect information 650 and control processing information.

Figure 22:
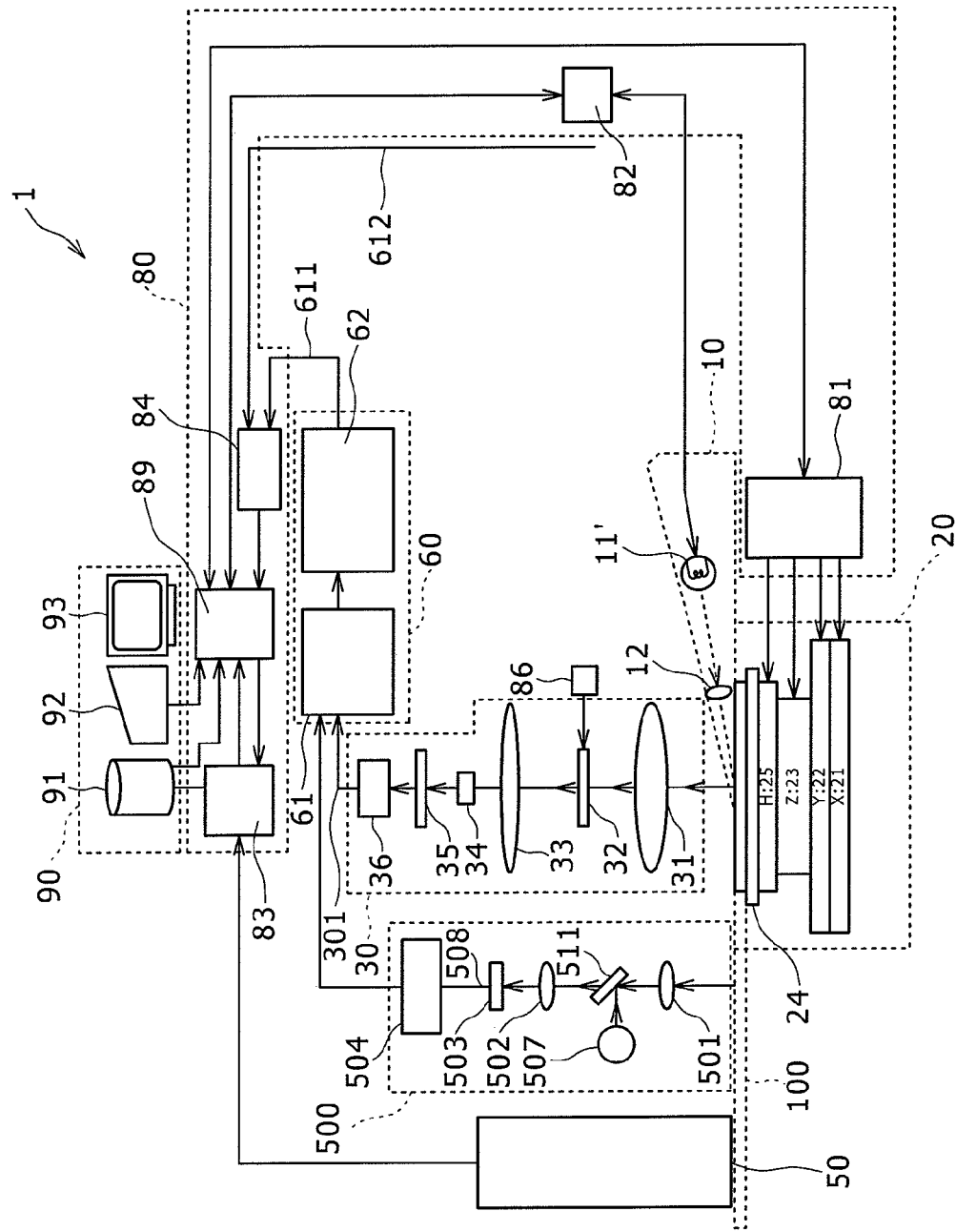
FIG. 22 shows a schematic configuration of the substrate inspection apparatus having a lamp as an illumination light source, and a TDI sensor as a photo sensor.
Figure 23:
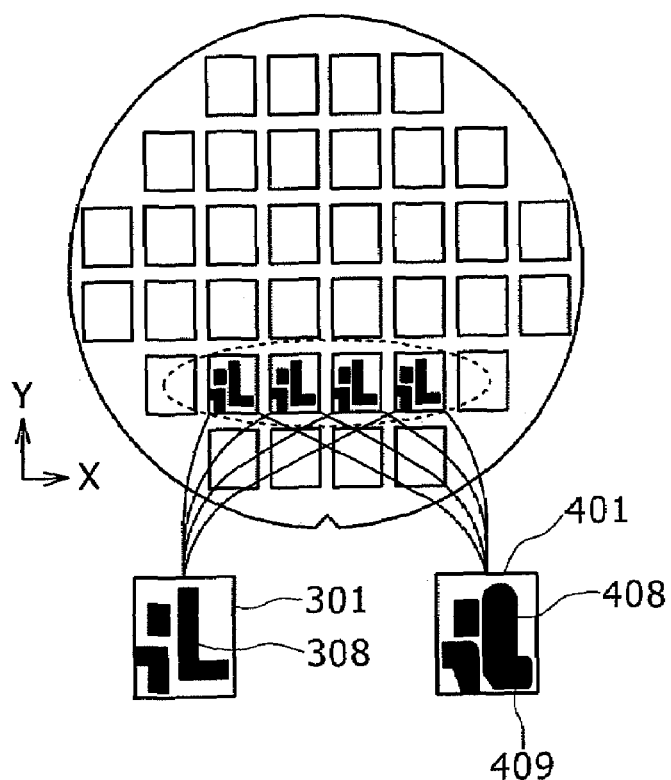
FIG. 23 is a drawing to show the relation between the chip layout of the substrate to be inspected and the image of the substrate surface imaged by the substrate inspection method in accordance with an embodiment of the present invention.

Referring to FIGS. 2, 3 and 23 to 26, the flow of the inspection is explained by the substrate inspection apparatus based on the embodiment of the present invention. Although the laser light source is used as the illumination light source in this embodiment, the illumination light source may be, for example, a lamp (FIG. 22).

Figure 2:
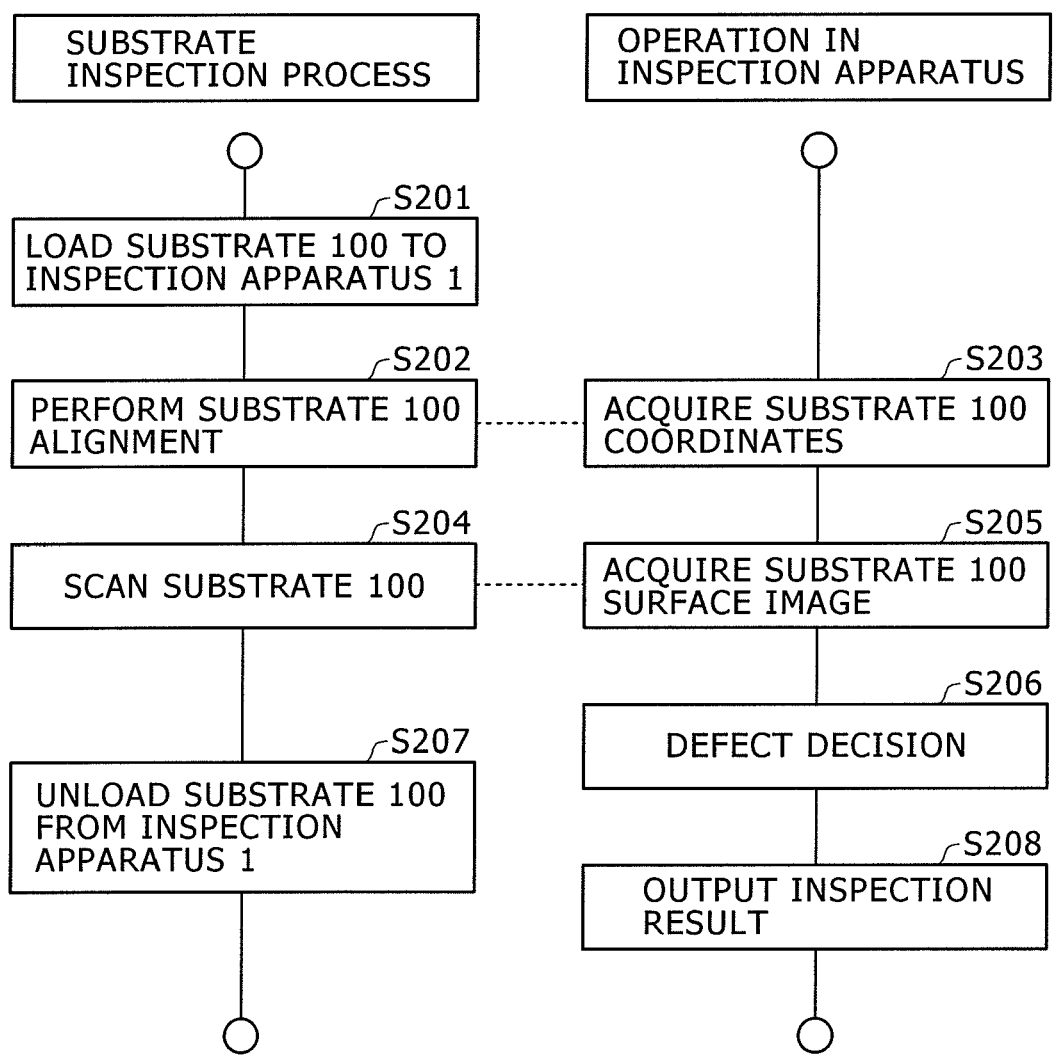
FIG. 2 is a flow diagram of the substrate inspection process of the inspection method in accordance with an embodiment of the present invention.
Figure 26:
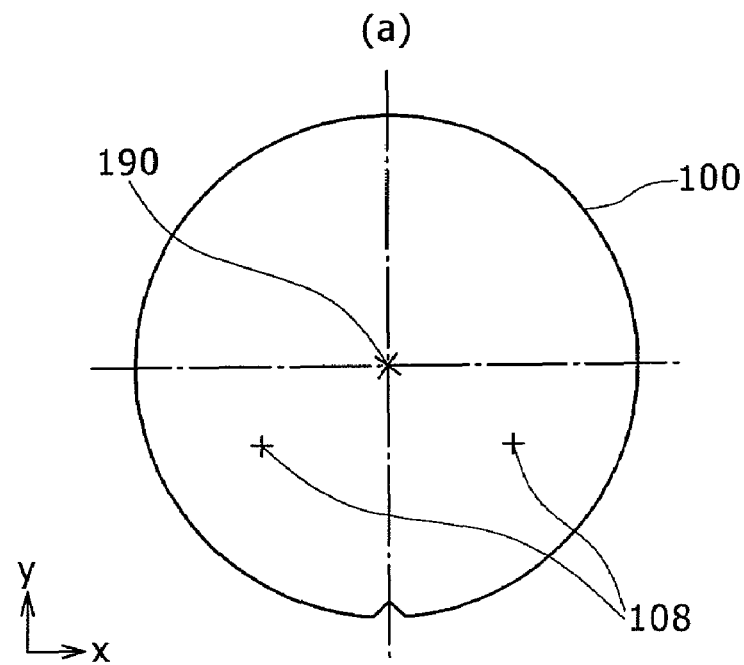
FIG. 26A is a drawing to show the state where the alignment of a wafer is completed.
FIG. 26B is a drawing to show the state before the alignment of a wafer is performed.
Figure 26:
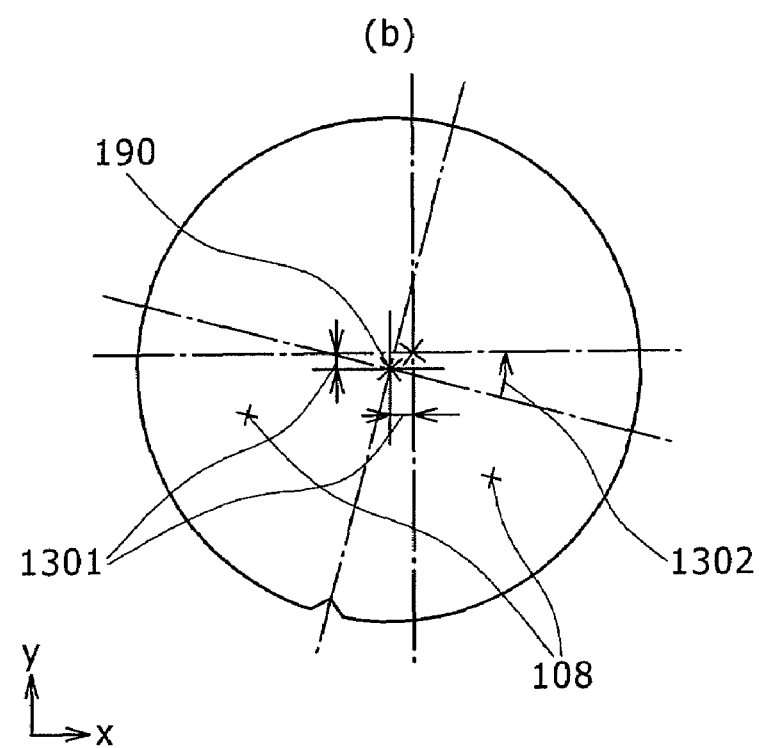

As first shown in FIG. 2, the substrate 100 is loaded to the inspection apparatus 1 (S201), and held by the substrate chuck 24. The inspection apparatus 1 performs alignment operation (S202) to correct inclination of the substrate 100 and to obtain the coordinates 190 of the wafer origin (S203) is (shown in FIG. 26, FIG. 26A shows the state where alignment is completed, and FIG. 26B shows the state before alignment).

Next, the substrate 100 is scanned (S204) and an optical image 301 (Refer to FIGS. 23 and 24) near the surface of substrate 100 is obtained (S205). Based on the obtained image, existence of a defect and a foreign substance is inspected by performing defect determination processing (S206) near the surface of substrate 100. As soon as the acquisition of optical image 301 near the surface is completed, the substrate 100 is unloaded from the inspection apparatus 1 (S207), and an inspection result is outputted (S208).

Figure 3:
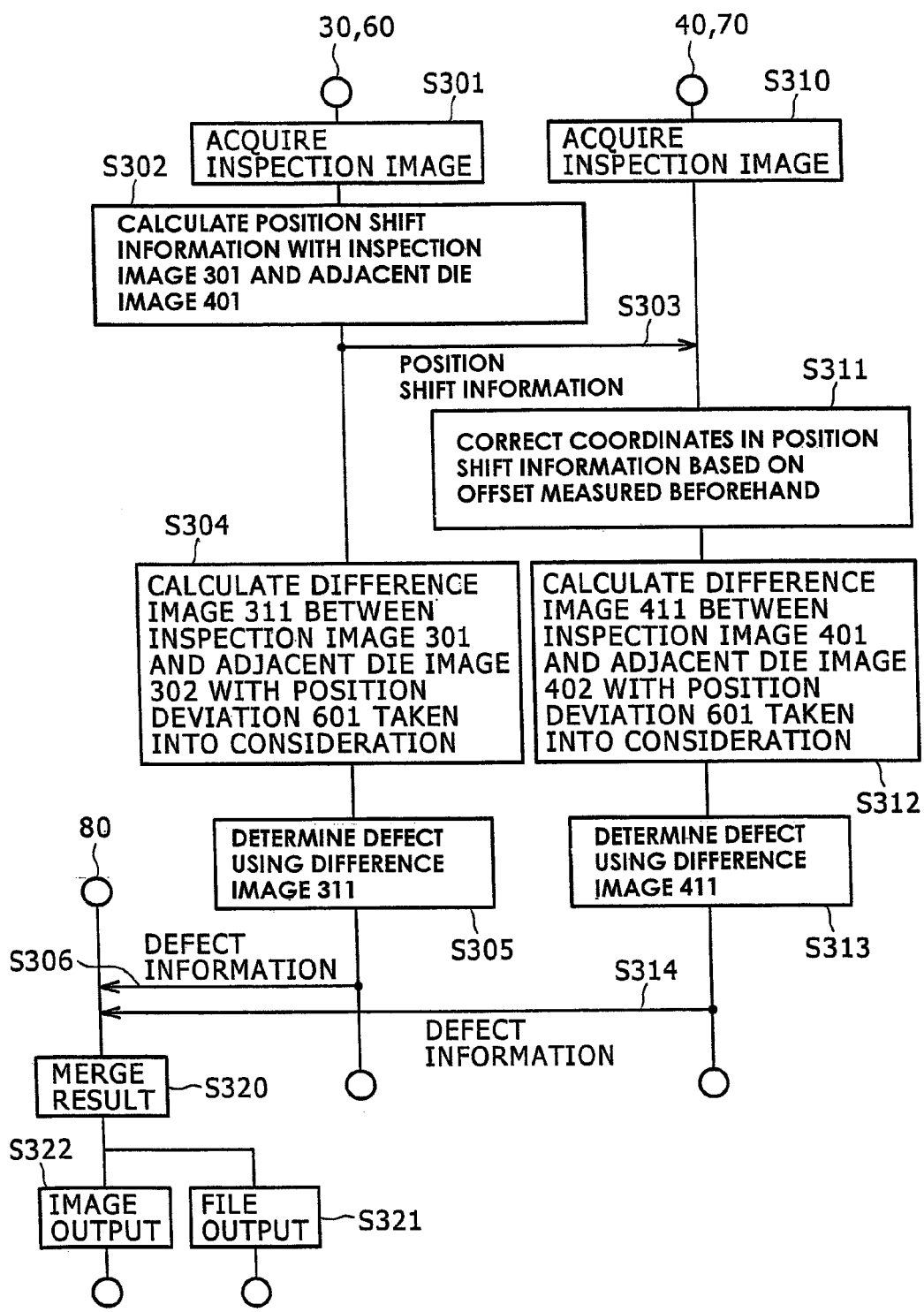
FIG. 3 is a flow diagram of the operation of a optical imaging system, an image processing system, and a control processing system of the inspection apparatus of test equipment among the flows of the substrate inspection process of a substrate inspection method.
Figure 4A:
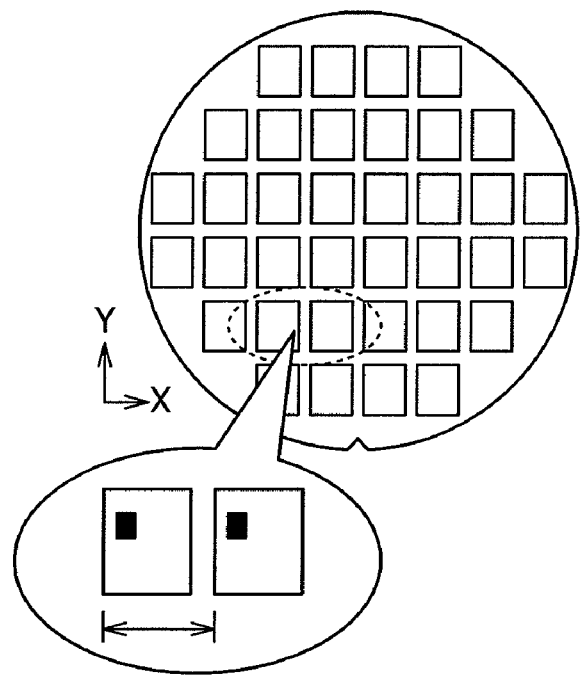
FIG. 4A shows the chip layout of the substrate to be inspected with the substrate inspection method in accordance with an embodiment of the present invention.
Figure 4B:
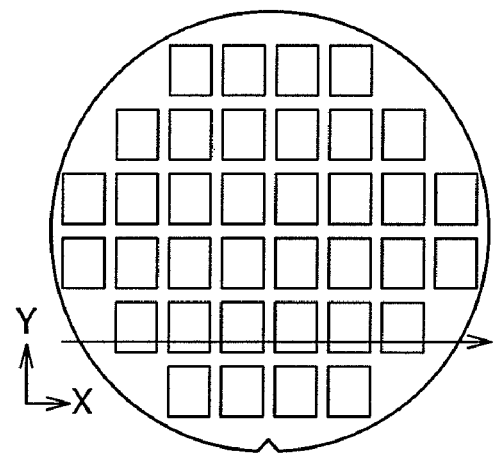
FIG. 4B shows a scanning direction for the chip substrate to be inspected with the substrate inspection method in accordance with an embodiment of the present invention.

Next, FIG. 3 shows the flow of operation of the first optical imaging system 30 and the first image processing system 60, the second optical imaging system 40 and the second image processing system 70, and the control processing system 80. The substrate 100 fixed to the substrate chuck 24 in the substrate scanning system 20 is scanned by the X direction stage 21. Synchronizing with the scanning, the surface image 301 and a surface image 401 of the substrate 100 are obtained by the first optical imaging system 30 and the second optical imaging system 40, respectively. Here it is assumed that the optical resolution of the first optical imaging system 30 is equal to or higher than the optical resolution of the second optical imaging system 40.

First, the flow of operation is described of the first optical imaging system 30 and the first image processing system 60.

Figure 25:
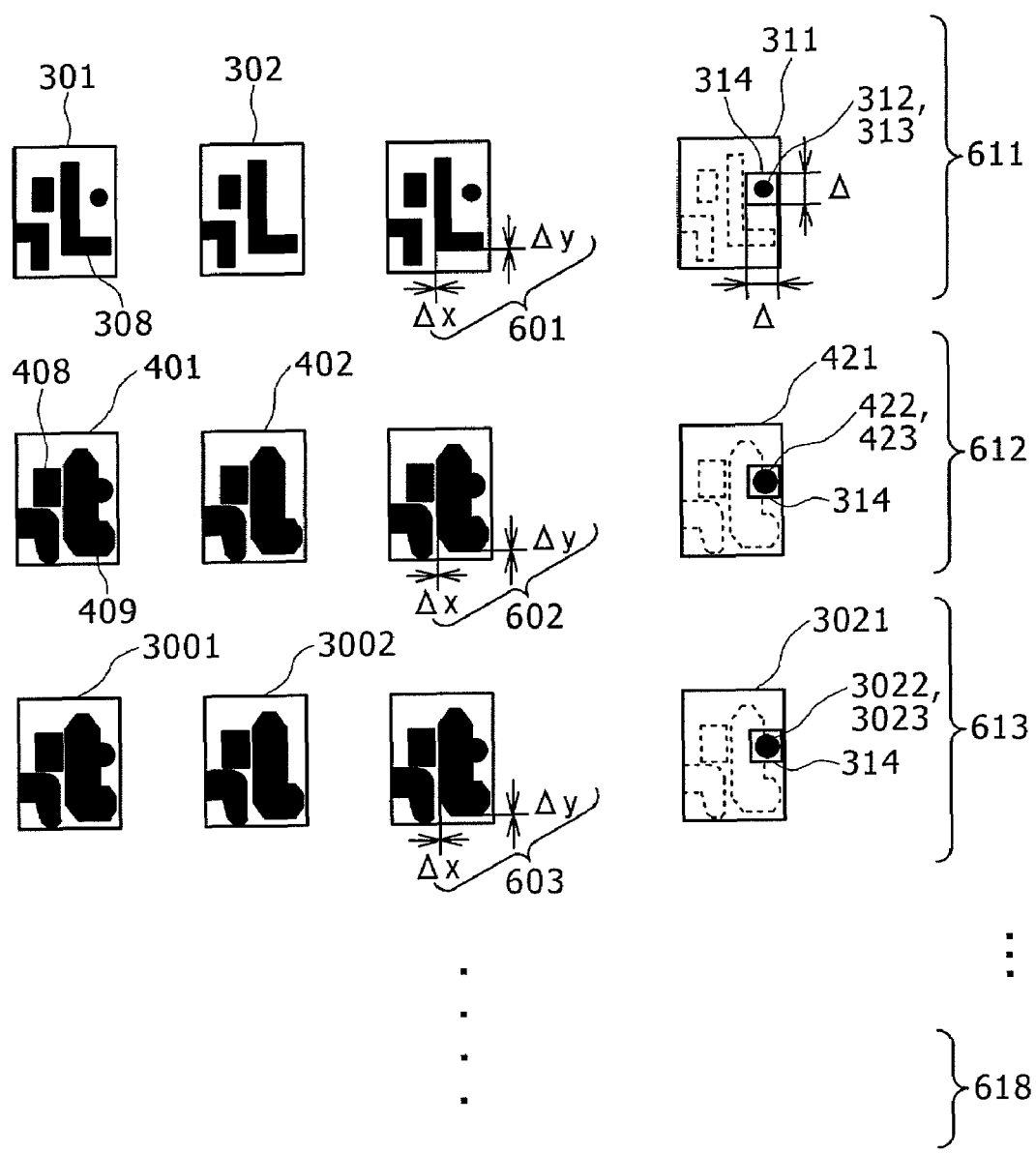
FIG. 25 is a drawing to explain false information obtained from the misalignment between the defect image and the reference image and difference image thereof in the substrate inspection method in accordance with an embodiment of the present invention.

The diffracted light and scattered light are produced with the surface of substrate 100 by illuminating the substrate 100 with the illuminating optical system 10, and a diffraction pattern produced by the scattered light from the repeated pattern on the substrate 100 are shaded with the spatial filter 32, and the scattered light from portions other than the repeated pattern is incident on the polarizing filter 34, and the transmitted light is detected by the photo sensor 35 of the first optical imaging system 30. The incident light on the photo sensor 35 is converted to electrons by photoelectric conversion and then converted again to a digital signal by the A/D- conversion unit 36, resulting in the surface image 301 (S301). The surface image 301 thus obtained is transmitted to the misalignment information calculation unit 61 between adjacent dies. As shown in FIG. 25, a misalignment 601 is produced between the surface image 301 and adjacent die image 302 as indicated in an image 303 obtained by superposition of two images. Calculation is made for this misalignment 601 by the misalignment information calculation unit 61 to a 1/10 pixel unit (S302), and the misalignment information thus obtained is transmitted together with center coordinates 308 of the image as misalignment information 610 to the misalignment information correction unit 71 of the second image processing system 70 (S303).

In the data processing unit 62 of the first image processing system 60, a difference image 311 between dies is calculated based on the surface image 301 and the misalignment information 610 between the adjacent dies calculated by the misalignment information calculation unit 61 (S304), and the defect determination and detection processing are performed using the calculated difference image 311 (S305). The processing result thus obtained is transmitted to the control processing system 80 as defect information 611 (S306). Although the defect information 611 includes at least a defect coordinate 312, it is preferable also to make a defect feature 313, a defect image 311, and an inspection image 301 into the defect information 611 collectively. The above is the flow of operation of the first optical imaging system 30 and the first image processing system 60.

Next, the flow of operation is described of the second optical imaging system 40 and the first image processing system 70. The diffracted light and scattered light are produced with the surface of substrate 100 by illuminating the substrate 100 with the illuminating optical system 10, and a diffraction pattern produced by the scattered light from the repeated pattern on the substrate 100 are shaded with the spatial filter 42, and the scattered light from portions other than the repeated pattern is incident on the polarizing filter 44, and the transmitted light is imaged on the photo sensor 45 of the second optical imaging system 40. The incident light on the photo sensor 45 is converted to electrons by photoelectric conversion and then converted again to a digital signal by the A/D-conversion unit 46, resulting in the surface image 401 (S310), which is sent to the image processing unit 72.

On the other hand, in the misalignment information correction unit 71 the misalignment information 610 transmitted from the misalignment information calculation unit 61 in the first image processing system 60 is corrected based on the calibration information obtained beforehand (S311), thus the misalignment information 620 after correction is obtained and sent to the image processing unit 72.

In the data processing unit 72, a difference image 411 between dies is calculated (S312) based on the surface image 401 outputted from the second optical imaging system 40 and the misalignment information 620 corrected by the misalignment information correction unit 71 and the defect determination and detection processing are performed using the calculated difference image 411 (S313). The processing result thus obtained is transmitted to the control processing system 80 as defect information 612 (S314). Although the defect information 612 includes at least the defect coordinate 312 as the defect information 611 does, it is preferable also to make the defect feature 313, the defect image 311, and the inspection image 301 into the defect information 611 collectively. The above is the flow of operation of the second optical imaging system 40 and the second image processing system 70.

Next, the flow of operation of control processing system 80 is described.

The defect information 611 and 612 transmitted from the first image processing system 60 and the second image processing system 70 are inspected for each defect using the coordinate information 312 and 412, and the same defect is decided. After merging the defect information for the same defect (S320), the merged information is outputted as file information through the input output means 92 and the accumulation means 91 (S321), or displayed on the screen 93 (S322).

The above is the flow of operation of the control processing system 80.

Figure 5:
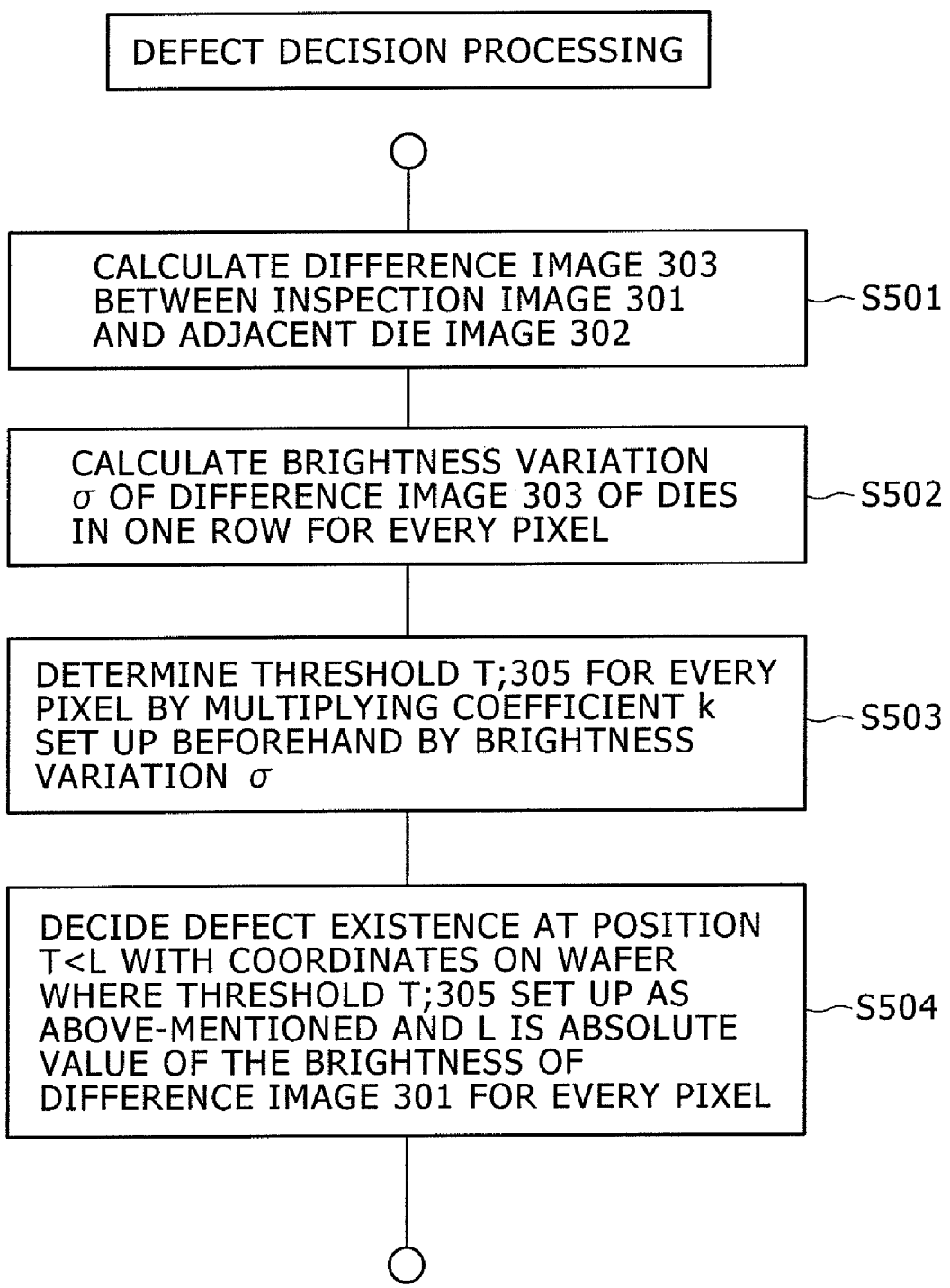
FIG. 5 is a flow diagram for the defect determination processing of the substrate inspection process by the substrate inspection method in accordance with an embodiment of the present invention.
Figure 24:
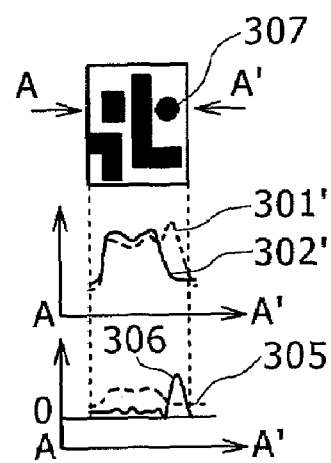
FIG. 24 is a drawing to illustrate the concept for performing a defect determination using the difference image between a defective image and a reference image and a statistical threshold in the substrate inspection method in accordance with an embodiment of the present invention.

Next, an example of the flow of defect determination processing is described referring to FIGS. 5, 24, and 25.

The calculation of difference images 311 between the inspection image 301 and the reference image 302 is made using the inspection image 301, the adjacent die image i.e. the reference image 302, and the misalignment information 610, and repeated (S501) by one X stage scan (hereafter referred to one row).

Next for every pixel, variation σ: 304 of the brightness is calculated of the portion corresponding to the identical parts of the difference image 311 for plural dies in one row (S502).

Then, a defect determination threshold T: 305 is determined (S503) for a watched pixel by multiplying a coefficient k set up beforehand using the user interface 90 by the above-mentioned brightness variation sigma: 304.

The defect determination threshold T: 305 thus determined is compared with the absolute value of the brightness of difference image 311 for every pixel and when the absolute value of the brightness of a difference image exceeds the defect determination threshold T: 305 (306), existence of a defect is concluded on the substrate 100 corresponding to the pixel position (S504).

The defect determination and a defect coordinate calculation are made on the substrate 100 for the inspection field of an image specified beforehand or all the inspection images obtained on the substrate 100 by repeatedly performing the flow of operation mentioned above.

In the above, after the difference image 311 between images of adjacent dies is obtained, the brightness variation 304 is calculated, and then the defective identification threshold 305 is obtained from the brightness variation 304, and a defect determination is performed based on the threshold 305. In defect determination a method is disclosed in JP-A-2003-83907, A where brightness of two adjacent images is combined and a difference image is calculated and a defect determination is performed as in the above-mentioned processing, or another method disclosed in JP-A-2003-271927, A is that a defect determination is performed based on the data voted for the multi-dimension space with axes having features such as brightness or contrast of an inspection image and a reference image. The above described methods and others wherein a defect determination is made using the difference information on brightness between dies are in accordance with an embodiment of the present invention.

Figure 6:
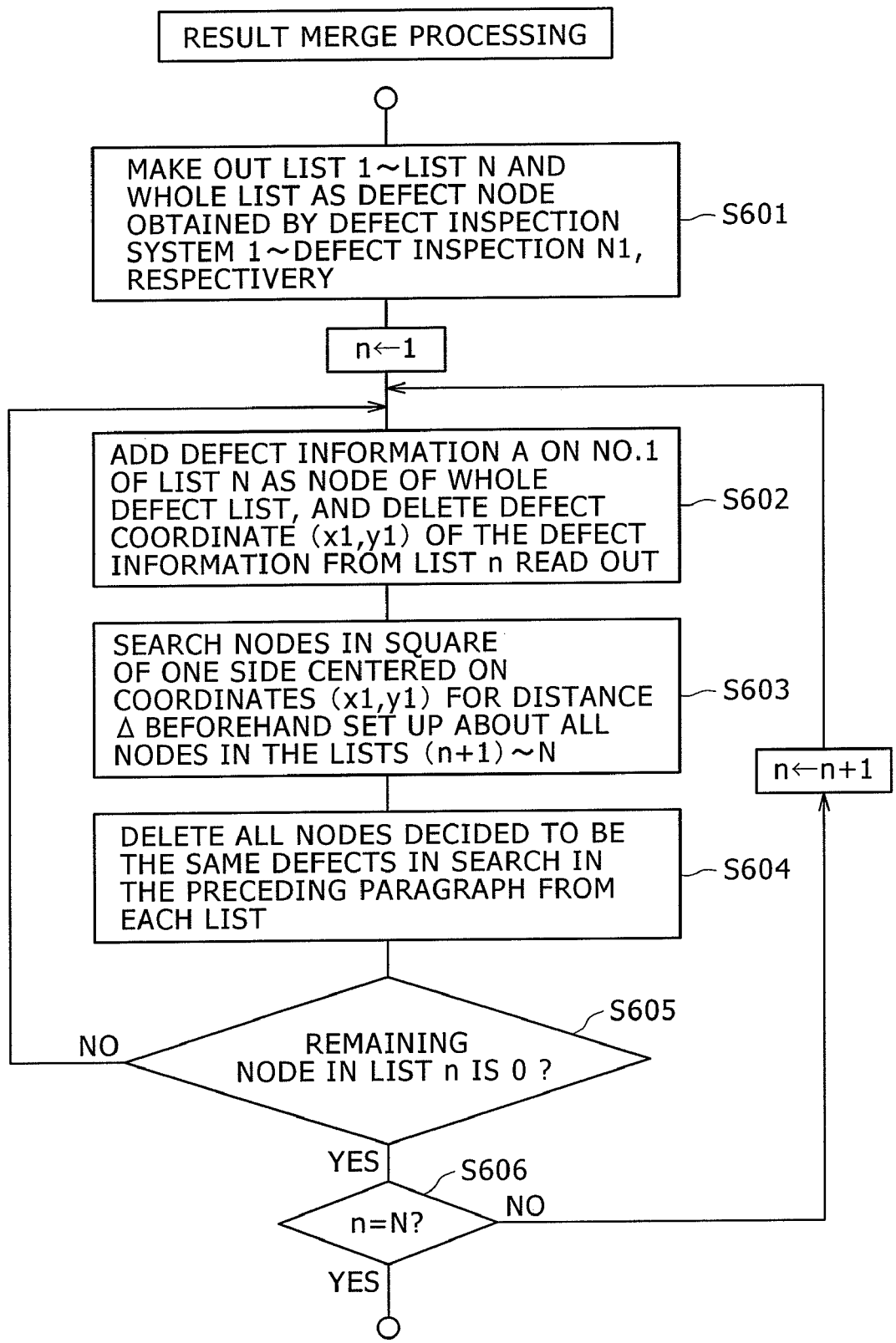
FIG. 6 is a flow diagram for a merge processing of the inspection result of the substrate inspection process by the substrate inspection method in accordance with an embodiment of the present invention.
Figure 27:
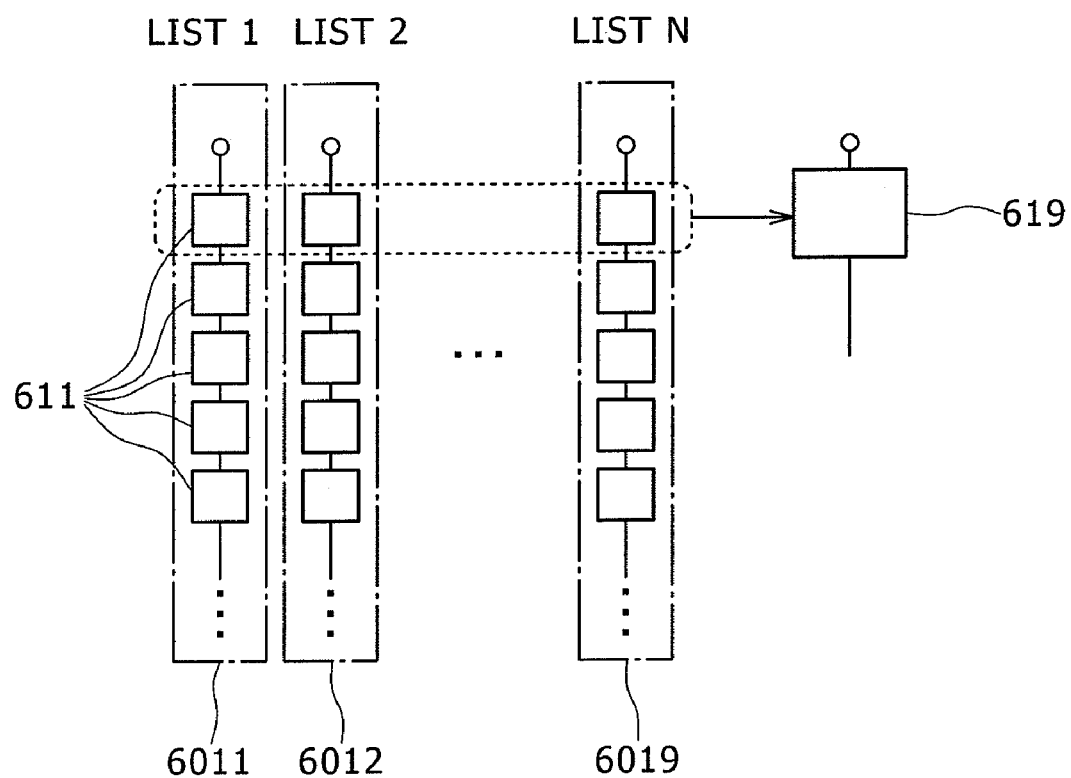
FIG. 27 is a drawing to illustrate the image of performing to merge the inspection result in the substrate inspection process in accordance with an embodiment of the present invention.

Next, the flow of merge processing of a defect determination result is described referring to FIG. 6 and FIG. 27.

The merge processing of a defect determination result is a procedure to put to one the same defect information detected in plural optical imaging systems.

Defect information lists 6011 to 6019 are created (S601) with defect information 6010 as a node obtained by plural optical imaging systems 1 to N (the first optical imaging system 30 and the second optical imaging system 40 in the composition of FIG. 1), respectively On this occasion, the following processing are more efficiently performed if the node is sorted by using the defect coordinate in defect information 6010 as a key.

First, the defect information A on the top of defect information list 6011 is added to the defect list 6020, and the defect information A is deleted from the defect information list 6011 (S602). Next, the defect information 6072 to 6079 of the coordinates which enter into a square 314 of one side Δ centering on the defect coordinate 6081 is searched for a distance Δ set up beforehand about the defect information list in which remaining nodes other than list 6011 exist (S603). If there is defect information corresponding to the above, the defect information is deleted from the defect information list noting that they are all due to the same defect, (S604).

The above procedure is repeated until the node of defect information list 6011 becomes empty (S605), and the same procedure is repeated also about the defect information list 6012 to 6019 successively (S606).

Next, the generation of the detection position offset value for each optical imaging system and the setup of calibration information are described referring to FIG. 7.

Figure 7A:
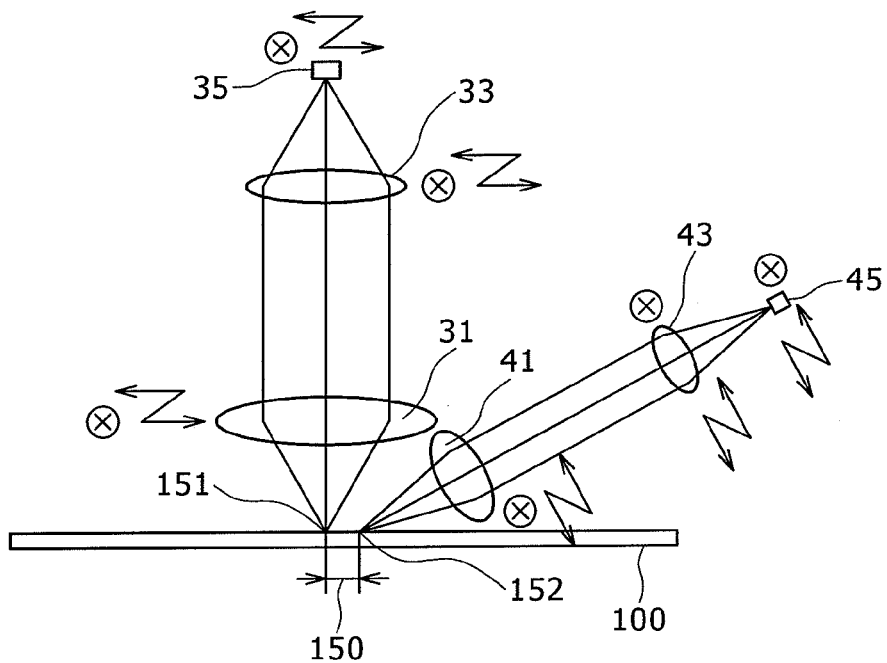
FIG. 7A shows generation of offset of a detection position for each optical imaging system in the substrate inspection process.

When the position of the optical components such as photo sensors 35, 45 and lenses 31, 33, 41, and 43 has a difference as shown in FIG. 7A, deviation 150 arises between the measuring points 151 and 152 of the first and the second optical imaging system 30, and 40 of the optical imaging systems on the surface positions, respectively, of the substrate 100 measured at a certain moment, wherein the measuring point 151, and 152 are the positions at which the center of the optical axis of the first optical imaging system 30 and the second optical imaging system 40 cross the surface of substrate 100, respectively. The misalignment information using the images between adjacent dies is about 1/10 of sensor pixel sizes, so that when converted into the size on the surface of substrate 100, the calculation accuracy becomes a size below 50 nm. It is necessary that the mechanical fine tuning of the above mentioned photo sensors and lenses be below 50 nm in order to make this misalignment 150 negligible, which is however, very difficult in practice.

Figure 7B:
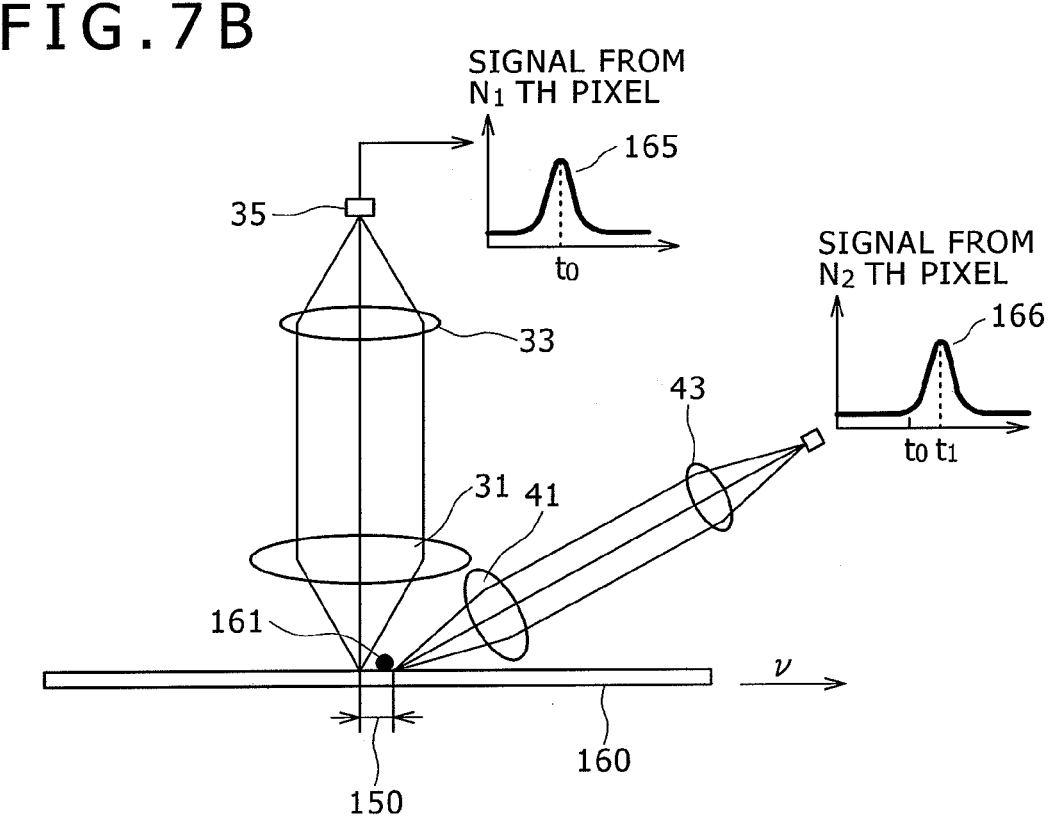
FIG. 7B shows the state of the detection signal due to the offset for each optical imaging system in the substrate inspection process.

So, in the present invention, this misalignment 150 is measured beforehand and using this measured information the position information 601 acquired in the first optical imaging system is corrected so that the alignment of the measurement image 401 of the second optical imaging system and the adjacent die image 402 are performed to merge. The procedure is as follows as shown in FIG. 7B.

The substrate 160 an isolated defect 161 of a PSL (polystyrene latex) particle etc. adhered thereon is held with the substrate chuck 24 of transfer system 20 and scanned.

In this state the surface of substrate 160 is illuminated by the illuminating optical system 10, and the scattered light from the isolated defect 161 is detected by the first optical imaging system 30 and the second optical imaging system 40, and the signal wave forms 165, 166 are outputted from each optical imaging system. Signal wave forms 165 and 166 outputted from the optical imaging systems each have the peaks at detection timings t0 and t1 from the scattered light from the defect, respectively. Since a deviation of this timing originates in the deviation 150 of the detection position of the first optical imaging system 30 and the second optical imaging system 40 on the substrate 160, the difference (t1−t0) is to be obtained. Denoting the substrate scan speed by v, the magnification by M1, M2 and pixel size p1, and p2 of each detection system, then the magnitude of misalignment is obtained to be v (t1−t0) in the scanning direction, and M2p2(N2−Nc1)−M1p1(N1−Nc1) in the a pixel line direction. Here, Nc1 is the normal coordinate and N1, N2 are the coordinates of the above-mentioned pixel, respectively.

Figure 8A:
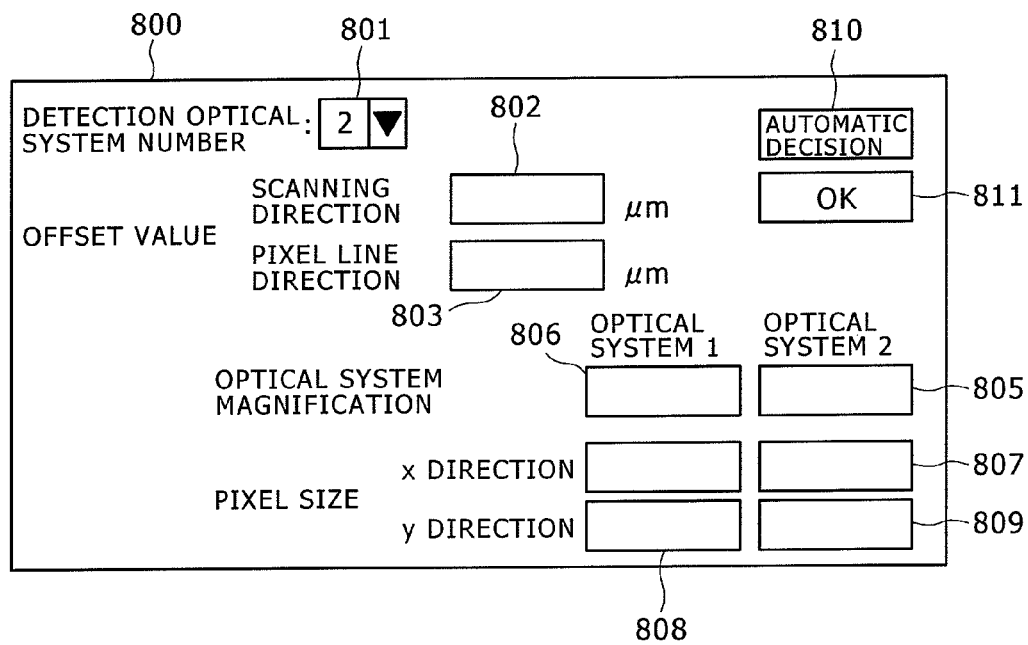
FIG. 8A shows an example of a user interface for calibrating the offset of a detection position for each optical imaging system in the substrate inspection apparatus.
Figure 8B:
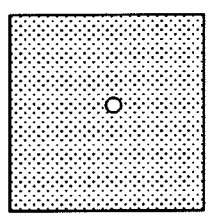
FIG. 8B shows an example of an image of the optical system 1 in the substrate inspection apparatus.
Figure 8C:
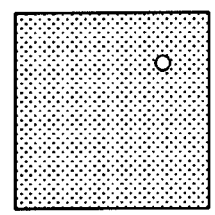
FIG. 8C shows an example of an image of the optical system 2 in the substrate inspection apparatus.

Next, FIG. 8 shows an example of GUI800 for performing the calibration of a display on the display section 93.

A optical imaging system number is set to the GUI800 first as 801 an offset value to be set thereon. When the offset values to the scanning direction and the pixel line direction are known, the values are directly inputted into a window 802 of the scanning direction, and a window 803 of the pixel line direction.

When this is not the case, corresponding values are inputted into the magnification windows 804, 805 and pixel size windows 806 to 809 of the optical systems 1 and 2, respectively, and an offset value is calculated in the defect information processing unit 84 by pushing automatic decision button 810.

In order to calculate an offset value, inside a device, images including a defect are acquired by scanning the substrate with an isolated defect such as a PSL particle adhered to the surface of the surface. In the defect information processing unit 84, the offset values in the scanning direction and the pixel line direction are automatically calculated using the defect coordinates of the acquired image, and the position information on the X stage 21 under scan.

This calculated offset values are displayed on the offset display columns 802 and 803 on GUI 800.

If a setup of each parameter is completed, a button 811 of 'O.K.' is pushed. Then a setup is completed. As explained above in an inspection apparatus including several optical imaging systems with different detection sensitivity. By calculating the offset value for each optical imaging system beforehand, it becomes possible to merge the information of the defect on the substrate detected by each optical imaging system, and it becomes possible to defect with higher sensitivity using more information.

Second Embodiment

Figure 9:
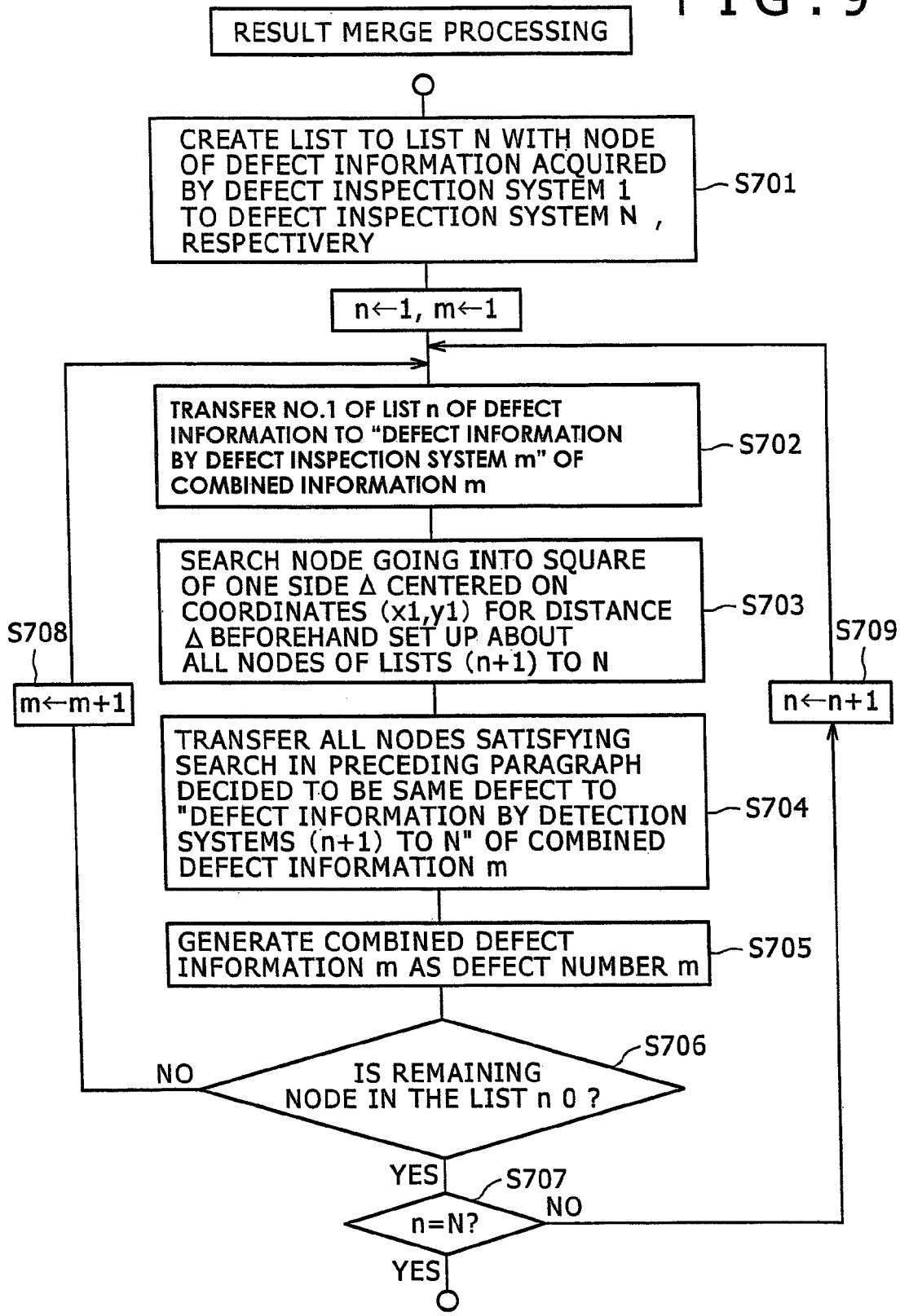
FIG. 9 is a flow diagram for a modified merge process as a result of the substrate inspection method.

The modification of the flow of the merge processing of the defect determination result shown in the first embodiment is explained using FIG. 9. The fundamental operation of each part in this embodiment is the same as in the first embodiment. Defect information lists 6011-6019 with the defect information 6010 as a node obtain by plural optical imaging systems 1 to N (the first optical imaging system 30 and second optical imaging system 40 in the configuration of FIG. 1), are produced, respectively (S701). In this case, the following processing is more efficiently performed if the node is sorted by using the defect coordinate in the defect information 6010 as a key.

First, defect information A on No. 1 of defect information list 6011 is copied to defect information 6191 by detection system 1 in integrated defect information 619, and defect information A is deleted from defect information list 6011 (S702). Suppose that the copy to this integrated defect information 619 and the procedure of deletion of defect information A are hereafter called as moving defect information A to integrated defect information 619.

Next, the defect information 6072-6079 with the coordinates entering into the square 314 of one side Δ with the center on the defect coordinate 6081 is searched for to a distance Δ set up beforehand about the defect information list in which the remaining nodes other than list 6011 exist (S703). If there is corresponding defect information they are transferred to the defect information 619 as the same defect to combine defect information 6072 to 6079 (S704). If the transfer is completed, the integrated defect information 619 is added to the combined defect list 6010 (S705).

The above procedure is successively repeated (S706) until the node of defect information list 6011 becomes empty, and the same procedure about the defect information list 602 to 6019 is repeated (S707, S709). The defective number of integrated defect information 6191 is kept from not overlapping with the one created by the procedure S705 thereby the defective number is increased by one for every S708.

Third Embodiment

Figure 19:
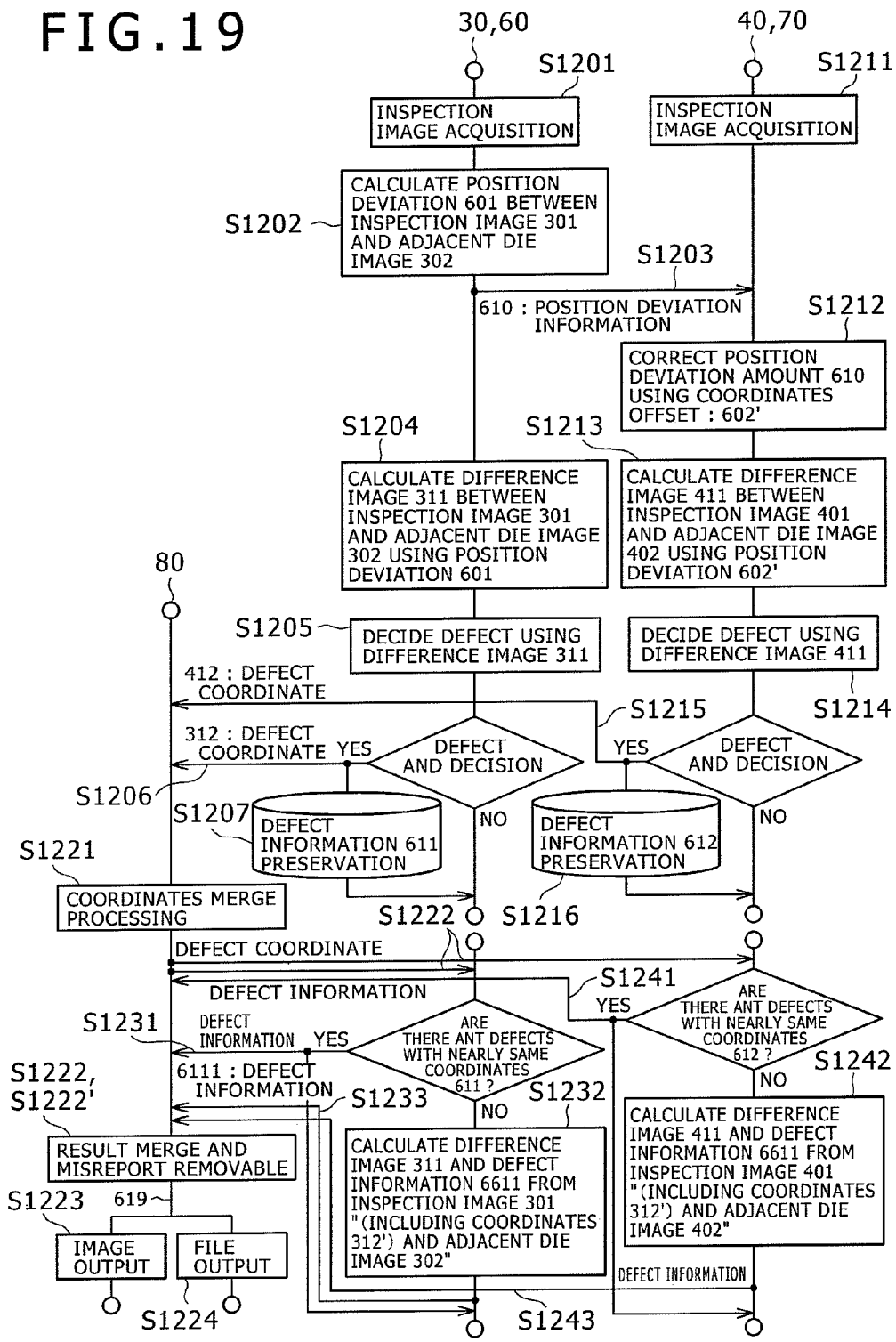
FIG. 19 is a flow diagram for the operation of the substrate inspection apparatus to perform removal processing of a false report.

Next, the flow of operation of a defect inspection system with a misreport removing function which is a modification of the flow of operation of the first embodiment is explained using FIGS. 19 and 27. The fundamental operation of each section in this embodiment is the same as in the first embodiment. The operation of the illuminating optical system 10, the substrate scanning system 20, the first optical imaging system 30, the second optical imaging system 40, and the focus measurement system 50 is the same as that of the first embodiment. Here, the flow of operation of the first image processing system 60, the second image processing system 70, and the control processing system 80 is shown.

The flow of operation of the first image processing system 60 is described first. A surface image 301 is obtained by the first optical imaging system (S1201). The surface image 301 obtained is sent to a misalignment information calculation unit 61 between adjacent dies. As shown in FIG. 25, misalignment 601 between the images produced between the surface image 301 and adjacent die image 302 is calculated to 1/10 pixel unit by the misalignment information calculation unit 61 (S1202), Together with center coordinates 308 of a image, the misalignment information is transmitted to the misalignment information correction unit 71 of the second image processing system 70 (S1203).

With data processing unit 62 of the first image processing system 60 the difference image 311 between dies is calculated (S1204) based on the front surface image 301 and the misalignment information 610 between the adjacent dies calculated by the misalignment information calculation unit 61, and the defect determination and detection processing are performed using this calculated difference image 311 (S1205). The defect coordinate 312 is transmitted to the control management system 80 among the obtained processing results (S1206). The obtained processing result is saved as defect information 611. Although defect information 611 includes at least the defect coordinate 312 it is also preferable to put the defect feature 313, the defect image 311, and the inspection image 301 into the defect information 611 collectively.

Next, the flow of operation of the second image processing system 70 is described.

The surface image 401 obtained by the second optical imaging system (S1211), is sent to image processing unit 72. On the other hand, the misalignment information correction unit 71 corrects the misalignment information 610 transmitted from the misalignment information calculation unit 61 in the first image processing system 60 based on the calibration information searched for beforehand (S1212) and sends to the image processing unit 72 after calculating misalignment information 602 correction.

The image processing unit 72, calculates the difference image 411 between dies based on the surface image 401 outputted from the second optical imaging system 40, the adjacent die image 402, and the misalignment information 602 corrected with misalignment information correction unit 71 (S1213), and performs the defect determination and detection processing using this difference image 411 (S1214). The acquired defect coordinate 412 is transmitted to the control processing system 80 (S1215). The obtained processing result is saved as defect information 612. Although defect information 612 includes at least the defect coordinate 412 it is also preferable to put the defect feature 413, the defect image 411, and the inspection image 401 into the defect information 612 collectively.

Finally, the flow of operation of the first image processing system 60, the second image processing system 70, and the control and processing system 80 is explained. The control and processing system 80 merges the wafer coordinates 312 of the defect received from the image processing unit 62 in the first image processing system 60, and the wafer coordinates 412 of the defect received from the image processing unit 72 in the second image processing system 10 (S1221). The method of merge is the same as the method of merging defect information in the flow operation of the control and processing system 80 in the first embodiment. The coordinate information 312 thus merged is transmitted to the image processing unit 62 in the first image processing system 60 and the image processing unit 72 in the second image processing system 70 (S1222).

The image processing unit 62 in the first image processing system 60 receives the defect coordinate 312' transmitted from the control processing system 80, and searches the defect information 611 with the coordinate information 312 which is mostly in agreement with the defect coordinate 312' out of the defect information saved. If the corresponding defect information 611 is saved, the defect information 611 is transmitted to the control processing system 80 (S1231), and the saved defect information 611 is deleted. When the corresponding defect information 611 is not saved, defect information 6611 is newly generated using inspection image 301" including the defect coordinate 312 and its adjacent die image 302" (S1232), and the defect information 6611 is transmitted to the control processing system 80 (S1233). The image processing unit 72 in the second image processing system 70 receives the defect coordinate 312' transmitted from the control processing system 80 and searches the defect information 612 with coordinate information 412 which is mostly in agreement with the defect coordinate 312' out of the defect information saved. If the corresponding defect information 612 is saved, the defect information 612 is transmitted to the control processing system 80 (S1241), and the saved defect information 612 is deleted. When the corresponding defect information 612 is not saved, Defect information 6612 is newly generated using the inspection image 401 containing the defect coordinate 312' and its adjacent die image 402 (S1242). The Defect information 6612 is transmitted to control processing system 80 (S1243). The control management system 80 generates the integrated defect information 619 using defect information 611 with defect coordinate 312' transmitted from the image processing unit 62 or 6611, and the defect information 612 with the defect coordinate 312' transmitted from image processing unit 72 or 6612 (S1241). In this case, when the defect information 6611 or 6612 are contained in the integrated defect information 619, the defect inspection result shown by the integrated defect information 619 is decided to be a misreport, and may be deleted (S222'). The integrated defect information 619 is outputted as file information through the input output means 92 and accumulation means 91 (S1223), or outputted as an image on the screen of display 93 (S1224).

Fourth Embodiment

Figure 10:
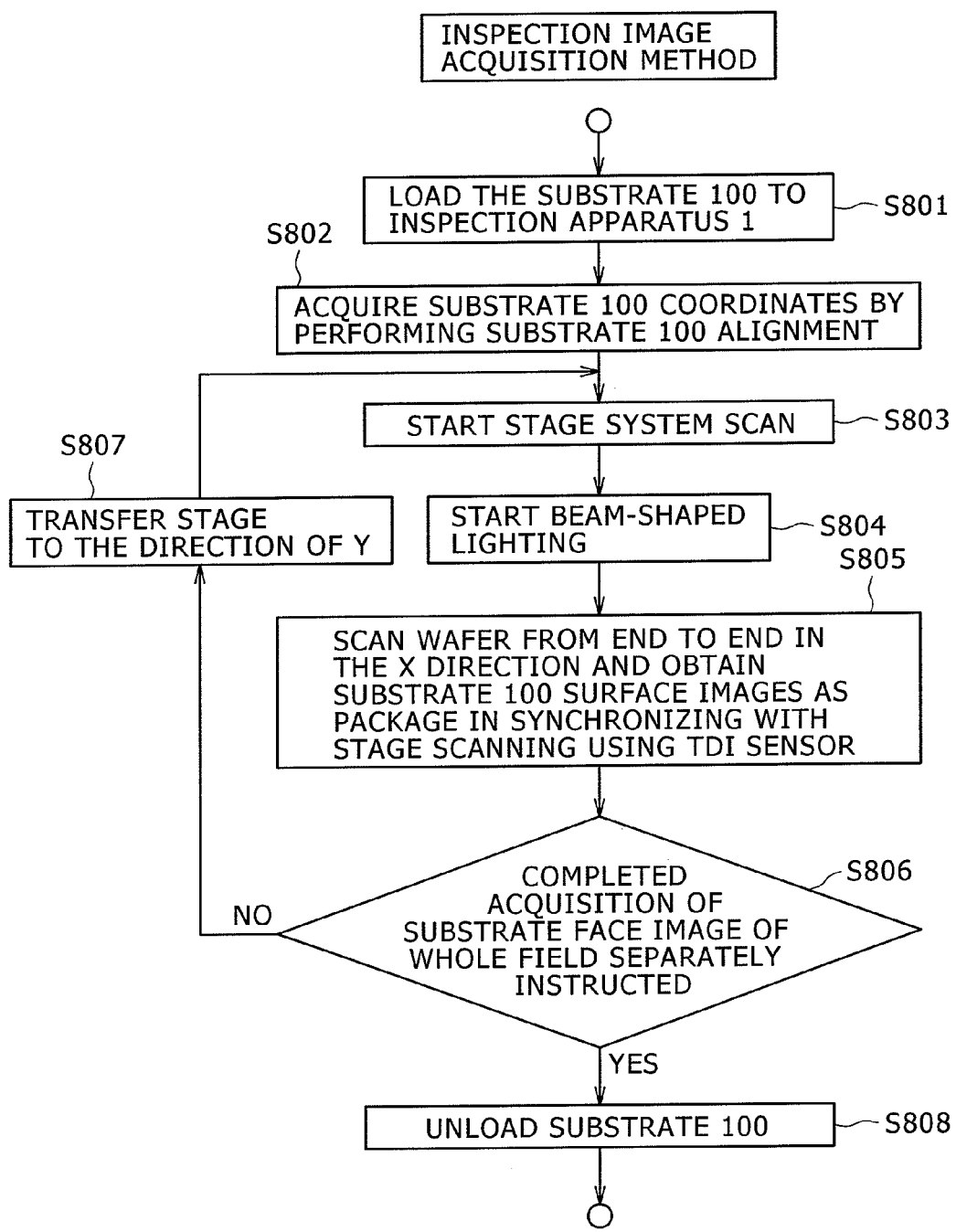
FIG. 10 is a flow diagram for the operation of the processing substrate illumination to a sheet shape and batch inspection using a two-dimensional photo sensor in the substrate inspection apparatus.

An example of modification of the first embodiment is explained using FIGS. 10 to 11 and FIG. 30. The configuration of apparatus is shown for the case of performing irradiation to the inspected substrate face with using the seat beam of FIG. 11 first, and detecting the inspection image of a substrate face using a TDI (Time Delay and integration) sensor. Here, a TDI sensor may be used although explanation is made that a one-dimensional sensor is used as a photo sensor.

Figure 11A:
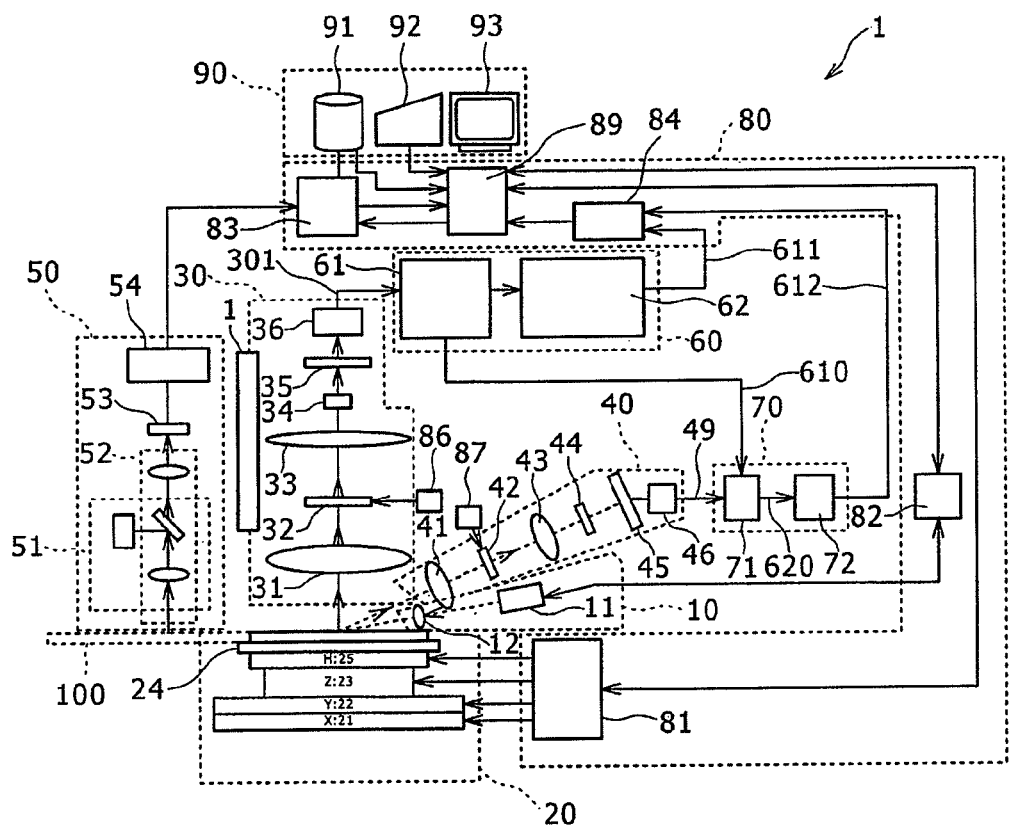
FIG. 11A shows a configuration of the substrate inspection apparatus in the case of performing batch inspection using a two-dimensional photo sensor by manufacturing a substrate illumination to a sheet shape.
Figure 11B:
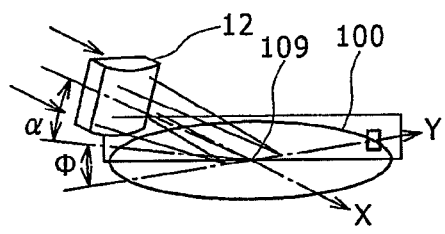
FIG. 11B shows an example of the optical lens in the case where the illumination-light incident on the illumination field with a sheet shape in the substrate from an oblique direction (direction inclined to the Y-axis by an angle of $\phi$)
Figure 11C:
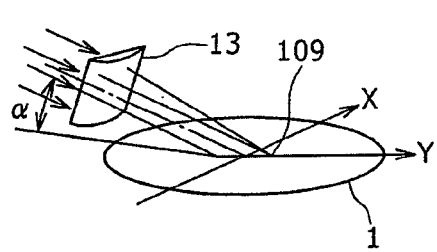
FIG. 11C shows another example of the optical lens in the case where the illumination-light incident on the illumination field with a sheet shape in the substrate from an longitudinal direction (the direction of the Y-axis.

For the above mentioned first embodiment, the illuminated surface field 109 of the substrate 100 is irradiated by the seat beam by using the cone lens 12 shown in FIG. 11B, or the cylindrical lens 13 shown in FIG. 11C as a beam shaping lens in the illuminating optical system 10 of FIG. 11A. To perform detection of the substrate face image of illuminated field 109 as a whole is enabled by using a one-dimensional sensor as the photosensor 35 of the first optical imaging system 30, and the photosensor 45 of the second optical imaging system 40. Next, the flow of operation for the case of performing seat beam lighting of the inspected substrate face using FIG. 10, and detecting the inspection image of a substrate face using a TDI sensor is shown. The operation of each section in this embodiment is fundamentally the same as explained in the first embodiment.

First, substrate 100 is loaded to the inspection apparatus 1, and the substrate 100 is fixed by the wafer chuck 34. Next, using an alignment mark 108 on the substrate 100, wafer alignment is performed, and the measurement is made on the offset 1301 and inclination 1302 of the coordinates on substrate 100 with the coordinates of a substrate scanning system.

When the inclination 1302 is larger than the angle threshold set up beforehand, after rotating the θ stage 26 to the opposite direction by the inclined angle and making it to about 0, alignment of the substrate is performed again and offset 1301 with the coordinates on the substrate 100 and the coordinates of a substrate scanning system is measured again. When the offset 1301 is larger than the offset threshold set up beforehand, X stage 21 and Y stage 22 are suitably moved so that the offset may be set to below offset threshold and nearly 0.

Next, the X stage 21 is scanned. While the wafer is irradiated by the seat beam 1310, the X stage 21 is moved at a uniform velocity mostly. In the range where the illuminated field irradiated by the seat beam is on the wafer, a shutter 13 of light source 11 opens, and performs sheet beam irradiation. The TDI sensor is operated in synchronization with the scan of the X stage 21, and acquire the surface image of substrate 100 collectively. When one scan of the X stage 21 is completed, the Y stage 22 is moved by the width which can be collectively measured with a photosensor and the scan of X stage 21 is repeated until the substrate face images of the whole measurement region on the substrate are acquired. When completed, the substrate 100 is unloaded and the operation of inspection apparatus is completed.

Fifth Embodiment

Next, the second embodiment of this invention is described according to FIG. 12 to 16.

Figure 12A:
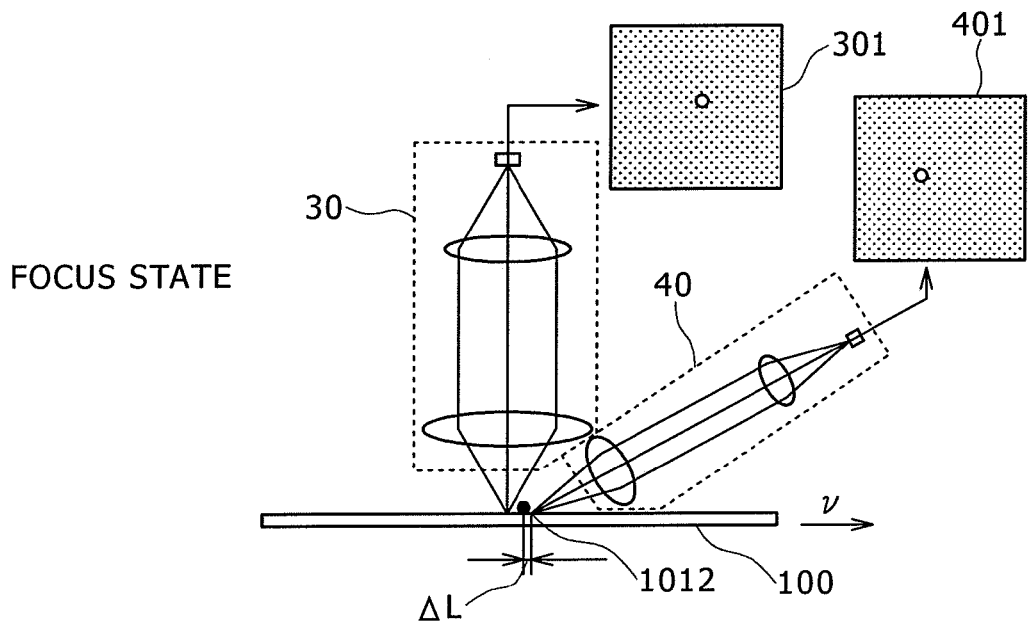
FIG. 12A shows a state where an upper detection system has an offset of detection position with respect to a substrate surface in the state of a focusing point for a slanting optical system.
Figure 12B:
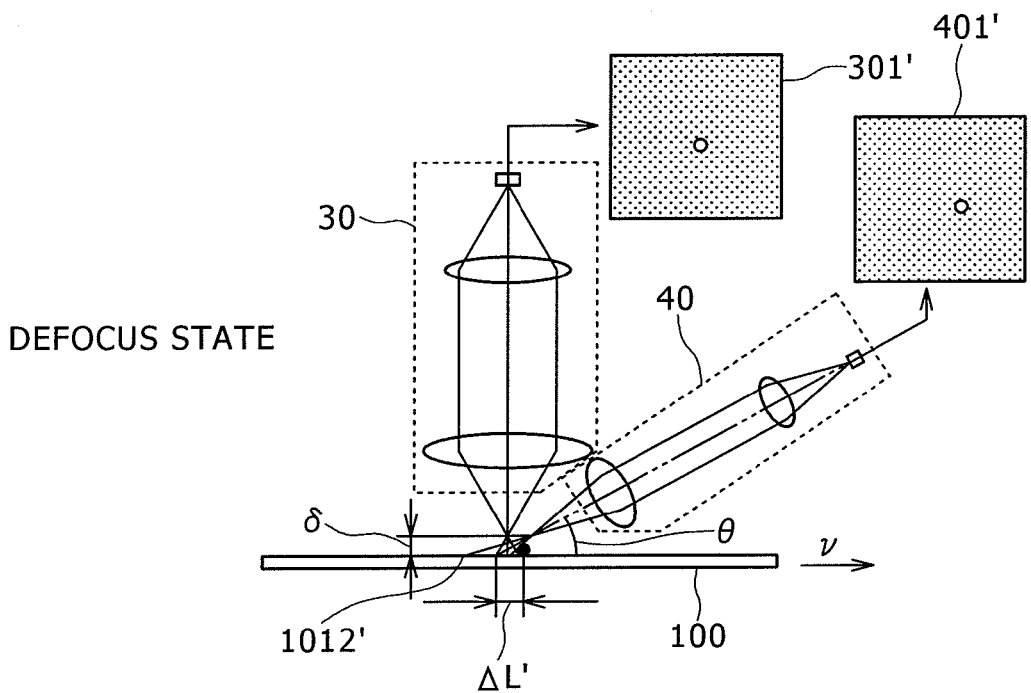
FIG. 12B shows a state where an upper detection system has an offset of detection position with respect to a substrate surface in the state of defocusing for a slanting optical system.
Figure 13:
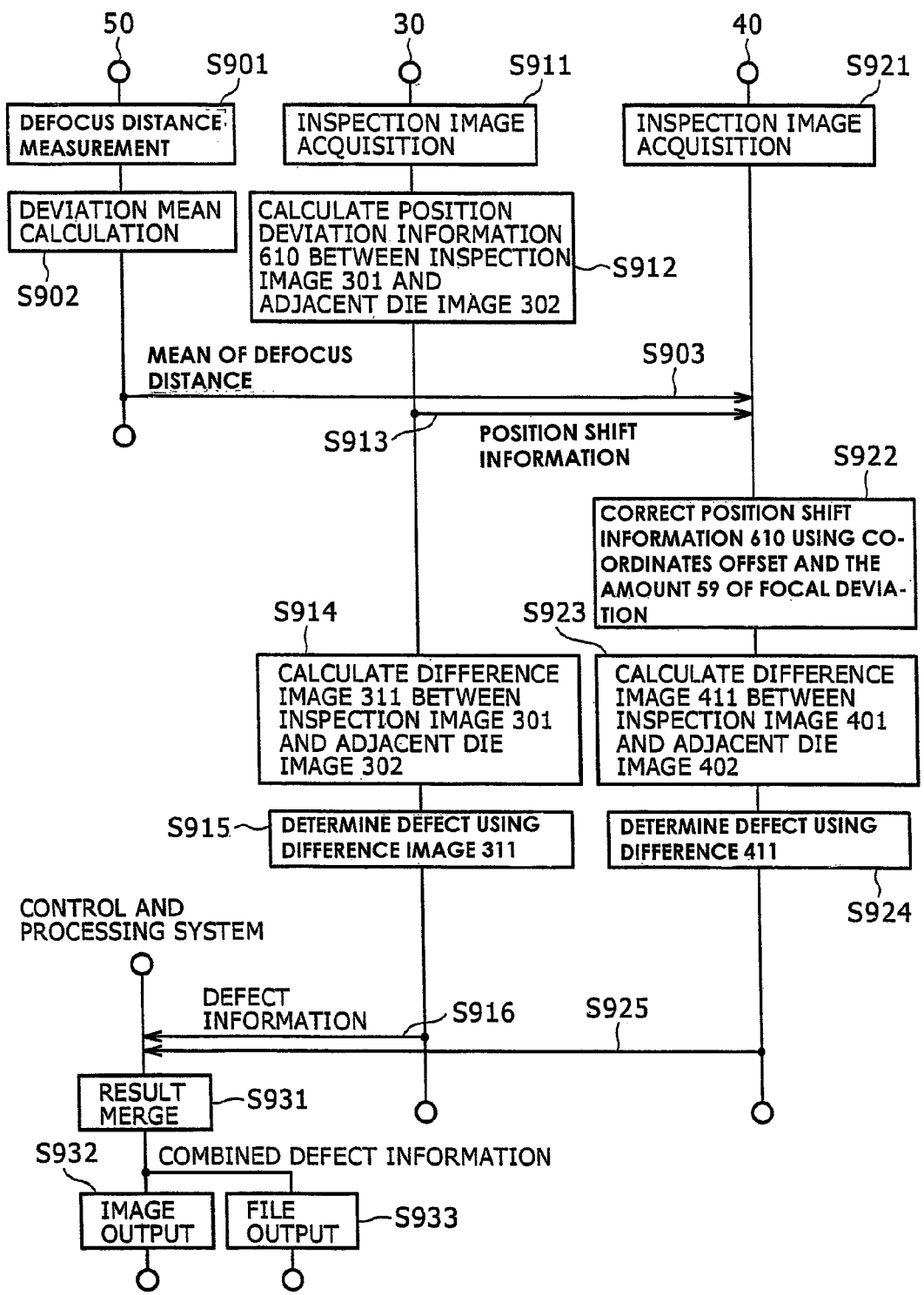
FIG. 13 is a flow diagram for the operation of the apparatus incorporating the correction operation for a misalignment of a slanting optical system arising from the defocusing with using defocusing measurement.

First, in the optical system (slanting detection system) the optical imaging system is inclined in the different direction from the normal line direction of the substrate face (hereafter called the method of slanting), a deviation is explained of the coordinates within a view with the coordinates on the wafer produced at the time of defocusing FIG. 12. In the optical imaging system (upper detection system in the following) whose normal line direction and the optical axis of the substrate face coincide practically, when a focus state changes, distribution of brightness fades, without the position of the brightest point changing (301→301'). In the method of slanting detection system, wafer coordinate 1012 corresponding to the point 1011 of a visual field center, for example changes depending on defocusing (401→401'). This is an essential deviation produced since a sensor detection side and the substrate face are not parallel, and unless defocusing is always 0, it is always produced. For example, if inclination of the slanting optical imaging system is set to θ and the amount of defocusing is set to δ, the deviation (ΔL'−ΔL) of the view point on the substrate 100 is given by $$(\Delta L' - \Delta L) = \delta / \sin \theta \quad (1).$$

So, in this embodiment, a procedure is provided to correct a deviation between the coordinates of the first optical imaging system and the second optical imaging system using the focal deviation value outputted from the focal system of measurement for performing automatic focusing operation. The signal line to transmit the amount of focal deviation 59 calculated in the focal system of measurement to misalignment information correction unit 71 is added in the second image processing system to the first embodiment.

Figure 14:
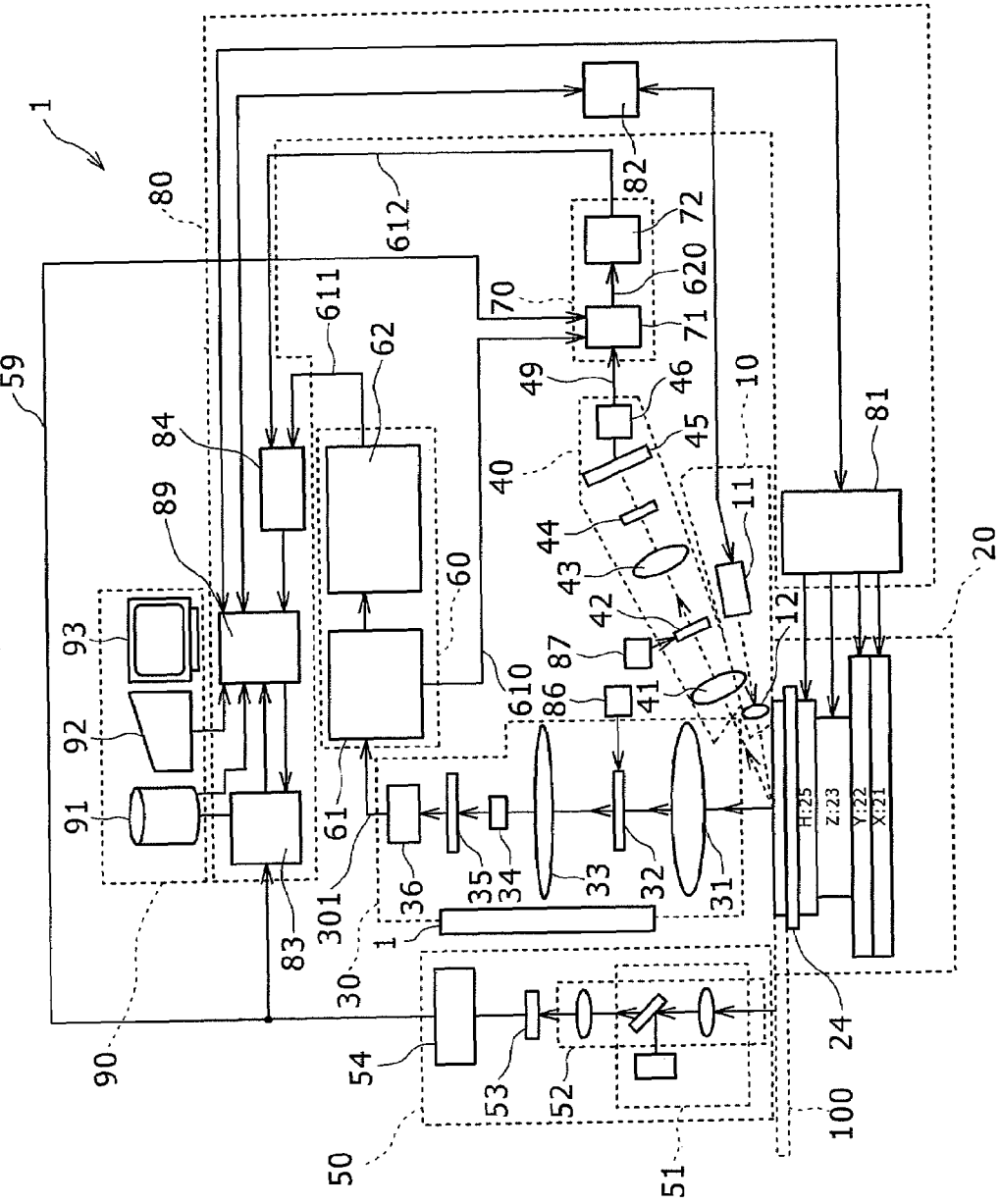
FIG. 14 shows a configuration of the substrate inspection apparatus in the case where correction operation is possible for a misalignment of the slanting optical system arising from defocusing defocusing measurement.

The configuration of apparatus for correcting the coordinates deviation resulting from defocusing in the slanting detection system of hereafter, and performing out defective decision and detection processing is shown in FIG. 14. The flow of defect determination and inspection processing is explained using FIG. 13 referring to using FIG. 14 about the slanting misalignment amount correction with defocusing measurement. However, the optical resolution of the first optical imaging system 30 is equal to or higher than the second optical imaging system 40 optical resolution, and that the first optical imaging system is an upward detection system, and the second optical imaging system is a slanting detection system. The flow of operation of focus measurement system 50 is explained first. The focus measurement system 50 calculates an average 59 of the focal deviation value over a long time of the measurement able to reduce a noise component, but not to exceed the cycle at which the image misalignment information between adjacency dies is calculated, and transmits the average 59 to the misalignment information correction unit 61 of the slanting second optical imaging system.

Next, the flow of operation is described of the first optical imaging system 30 and the first image processing system 60. The fundamental operation of each part in this embodiment is the same as in the first embodiment. The diffracted light and scattered light produced on the surface of the substrate 100 are converted to the current by the photoelectric conversion and A/D conversion in the photosensor 35 in the first optical imaging system 30, and produce a surface image 301. The surface image 301 thus obtained is transmitted to the misalignment information calculation unit 61 between adjacent dies. Calculation is made for this misalignment 610 by the misalignment information calculation unit 61 to a ¹⁄₁₀ pixel unit, and the misalignment information 610 thus obtained is transmitted to the correction unit 71 in the second image processing system 70. In the data processing unit of the first image processing system 60, a difference image 311 between dies is calculated based on the surface image 301 and the misalignment information 601 between the adjacent dies, and the defect determination and detection processing are performed using the calculated difference image 311. The processing result thus obtained is transmitted to the control processing system 80 as defect information 611. Although the defect information 611 includes at least a defect coordinate 312, it is preferable also to make a defect feature 313, a defect image 311, and an inspection image 301 into the defect information 611 collectively. The above is the flow of operation of the first optical imaging system 30 and the first image processing system 60.

Next, the flow of operation is described of the second optical imaging system 40 and the first image processing system 70. The diffracted light and scattered light are produced with the surface of substrate 100 by illuminating the substrate 100 with the illuminating optical system 10, and a diffraction pattern produced by the scattered light from the repeated pattern on the substrate 100 are shaded with the spatial filter 42, and the scattered light from portions other than the repeated pattern is incident on the polarizing filter 44, and the transmitted light is imaged on the photo sensor 45 of the second optical imaging system 40. The incident light on the photo sensor 45 is converted to electrons by photoelectric conversion and then converted again to a digital signal by the A/D-conversion unit 46, resulting in the surface image 401 (S310), which is sent to the image processing unit 72.

In the misalignment information correction unit 71 the misalignment information 610 transmitted from the misalignment information calculation unit 61 in the first image processing system 60 is corrected based on the calibration information measured beforehand, thus the misalignment information 620 is obtained and sent to the image processing unit 72. In the data processing unit 72, a difference image 411 between dies is calculated based on the surface image 401 and the corrected misalignment information 620 and the defect determination and detection processing are performed using the calculated difference image 411. The processing result thus obtained is transmitted to the control processing system 80 as defect information 612. Although the defect information 612 includes at least the defect coordinate 412, it is preferable also to make the defect feature 413, the defect image 411, and the inspection image 401 into the defect information 611 collectively. The above is the flow of operation of the second optical imaging system 40 and the second image processing system 70.

Next, the flow of operation of control processing system 80 is described. The defect information 611 and 612 transmitted from the first image processing system 60 and the second image processing system 70 are inspected for each defect using the coordinate information 312 and 412, and the same defect is decided. After merging the defect information for the same defect, integrated defect information 619 is generated. The integrated defect information 619 is outputted as file information through the input output means 92 and the accumulation means 91, or displayed on the screen 93.

Sixth Embodiment

Figure 15:
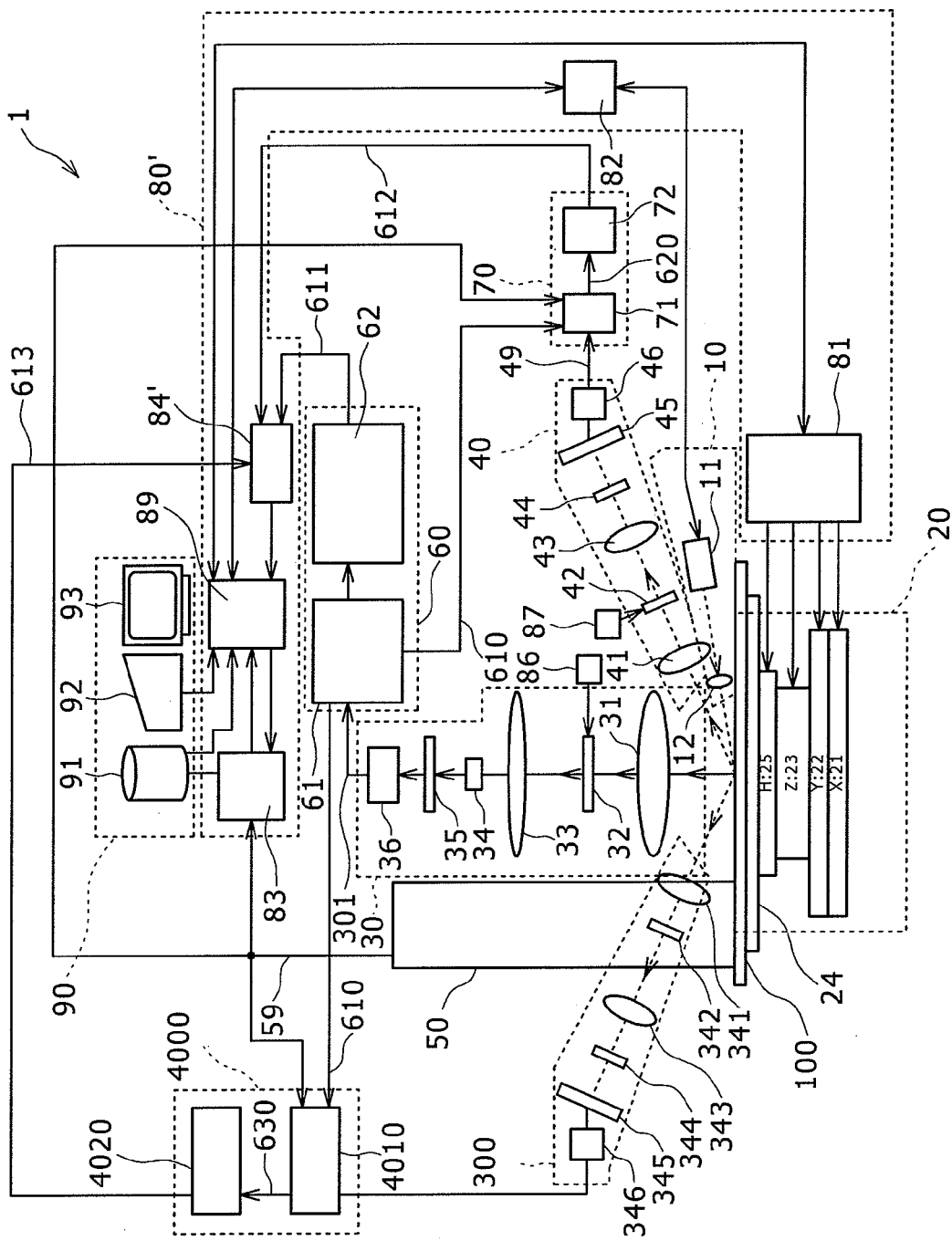
FIG. 15 shows a configuration of the substrate inspection apparatus in the case where three systems (hereafter called an inspection head) are provided using the defect optical imaging system and the detected images obtained therewith.
Figure 16:
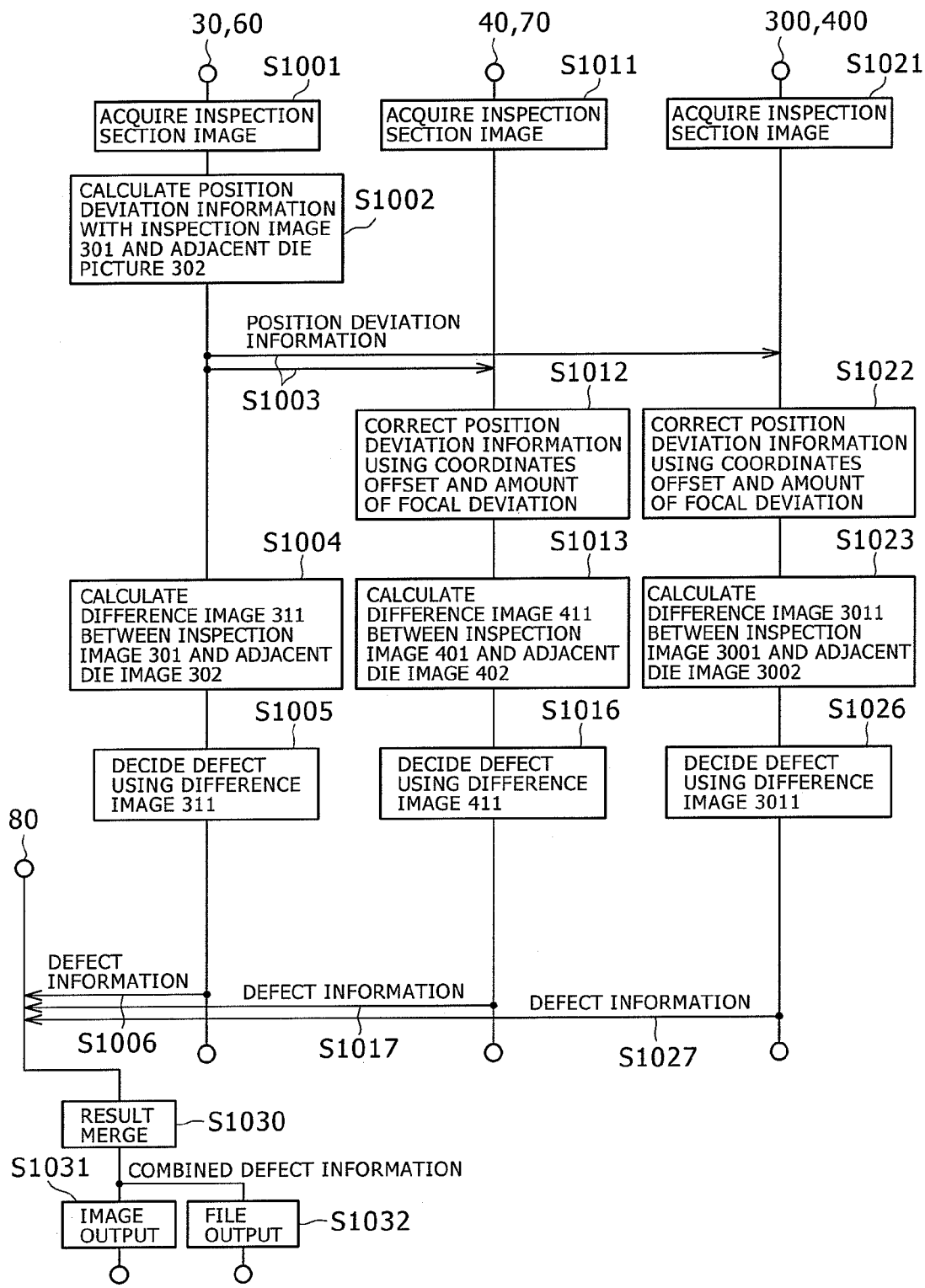
FIG. 16 is a flow diagram for the operation of the substrate inspection apparatus having three inspection heads.

Next, the composition of a defect inspection system with three optical imaging systems which is another modification of the first embodiment and the flow of operation thereof are explained using FIGS. 15 and 16, respectively.

A third optical imaging system 300 and a third image processing system 400 for processing the output thereof are added to the first embodiment. The misalignment information correction unit 410 of the third image processing system 400 can receive the alignment information 610 from the first misalignment information calculation unit 61 similarly to the misalignment information correction unit 71 of the second image processing system 70 explained in the first embodiment.

The flow of operation is shown of the first optical imaging system 30 with the first image processing system 60, the second optical imaging system 40 with the second image processing system 70, and the third optical imaging system 300 with the third image processing system 400, together with the control processing system 80. The same number in this embodiment as that in the first embodiment shows similar function and operation.

The semiconductor substrate 100 fixed to the wafer chuck 34 of the substrate scanning system 30 is scanned by the X direction stage 31, surface images 301, 401, and 3001 of substrate 100 are obtained in synchronization with the scanning, by the first optical imaging system 30, second optical imaging system 40, and third optical imaging system 300, respectively. Here the optical resolution of the first optical imaging system 30 is equal to or higher than the optical resolution of the second optical imaging system 40, and also the optical resolution of the third optical imaging system 300.

The flow of operation of the first optical imaging system 30 and the first image processing system 60, and the flow of operation of the second optical imaging system 40, and the second image processing system 70, are the same as those explained in the first embodiment and omitted here.

Next, the flow of operation is described of the third optical imaging system 300 and the third image processing system 4000. The fundamental operation is the same as the operation flow of the second optical imaging system 40 and the second image processing system 70.

The diffracted light and scattered light produced on the surface of the substrate 100 are converted to the current by the photoelectric conversion and A/D conversion in the photosensor 35 by the 3ird optical imaging system 300, and produce a surface image 3001, which is transmitted to a data processing unit 4020 for performing the defect determination and processing using the difference image between dies of image processing system 4000.

On the other hand, the misalignment information correction unit 4010 corrects the misalignment information 610 transmitted from the misalignment information calculation unit 61 of the first image processing system 60 based on the calibration information set up beforehand and calculates the misalignment information 630 after correction, and then sends the misalignment information 630 to the data processing unit 4020.

In the data processing unit 4020, a difference image 3011 between dies is calculated based on the surface image 3001 and the corrected misalignment information 630 and the defect determination and detection processing are performed using the calculated difference image 3011. The processing result thus obtained is stored as the defect information 613. Although the defect information 613 includes at least the defect coordinate 3012, it is preferable also to make the defect feature 3013, the defect image 3011, and the inspection image 3001 into the defect information 613 collectively. The above is the flow of operation of the third optical imaging system 300 and the third image processing system 400.

Next, the flow of operation of control processing system 80' is described.

The fundamental operation of control processing system 80' is the same as in the first embodiment. The defect information 611, 612, and 613 transmitted from the first image processing system 60, the second image processing system 70, and the third image processing system 400 are merged using the coordinate information 611, 612, and 613 contained in each defect information, to be the same defect and an integrated defect information 619 is generated. Integrated defect information 619 is outputted through input output means 92 and accumulation means 91. The above is the operation flow of the control processing system 80'.

In this embodiment, although an example of the inspection apparatus is shown including three optical imaging system with different detection sensitivities from one another, however, as explained in the first embodiment also in this embodiment, by the offset value between each optical imaging system is calculated beforehand, It becomes possible to merge the information on the defect on the substrate detected by each optical imaging system, and to defect with higher sensitivity using more information.

Seventh Embodiment

Figure 17:
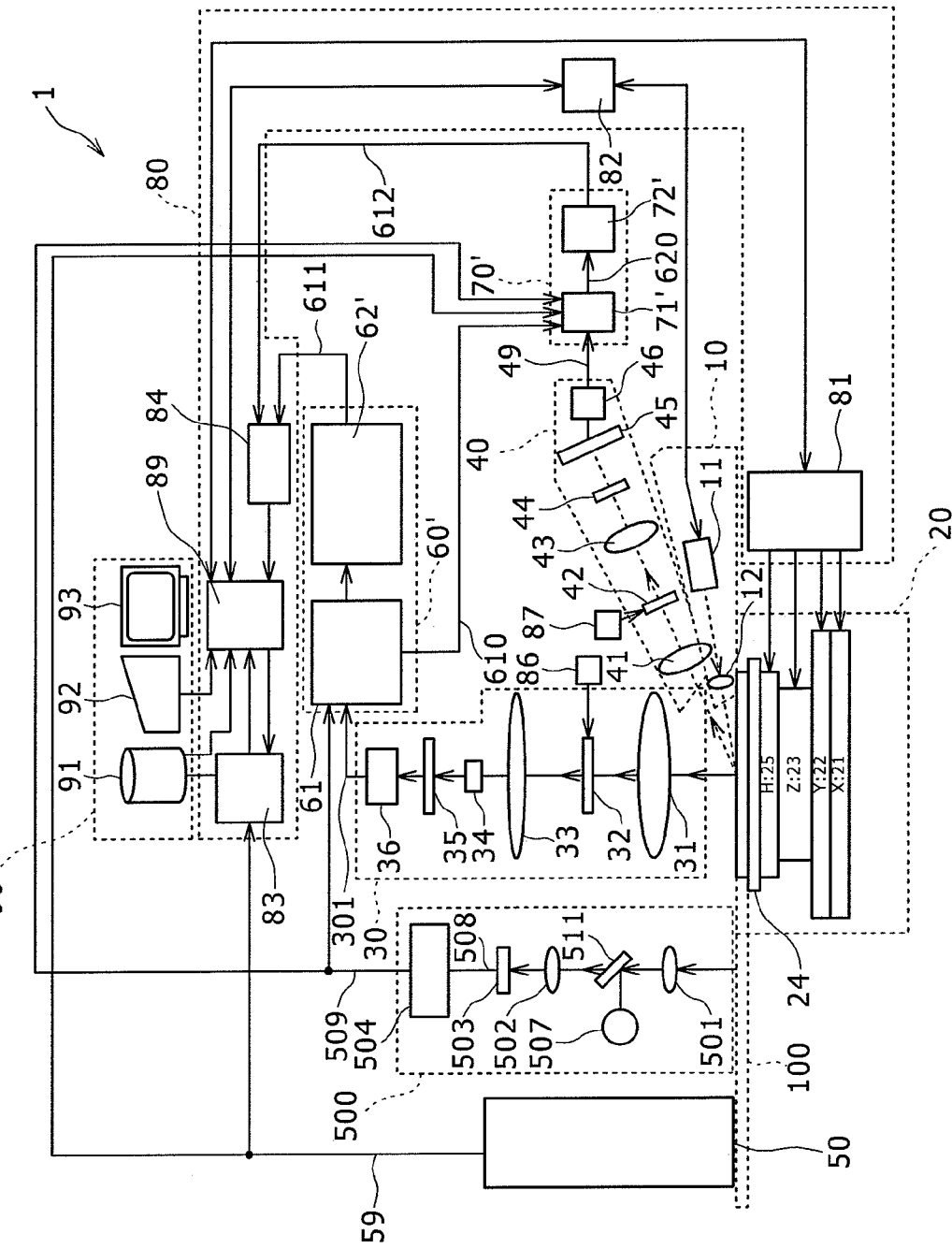
FIG. 17 shows a configuration of the substrate inspection apparatus in the case where two inspection heads and an image optical imaging system (having a bright field/white dark field) are provided for merged deviation calculation.
Figure 18A:
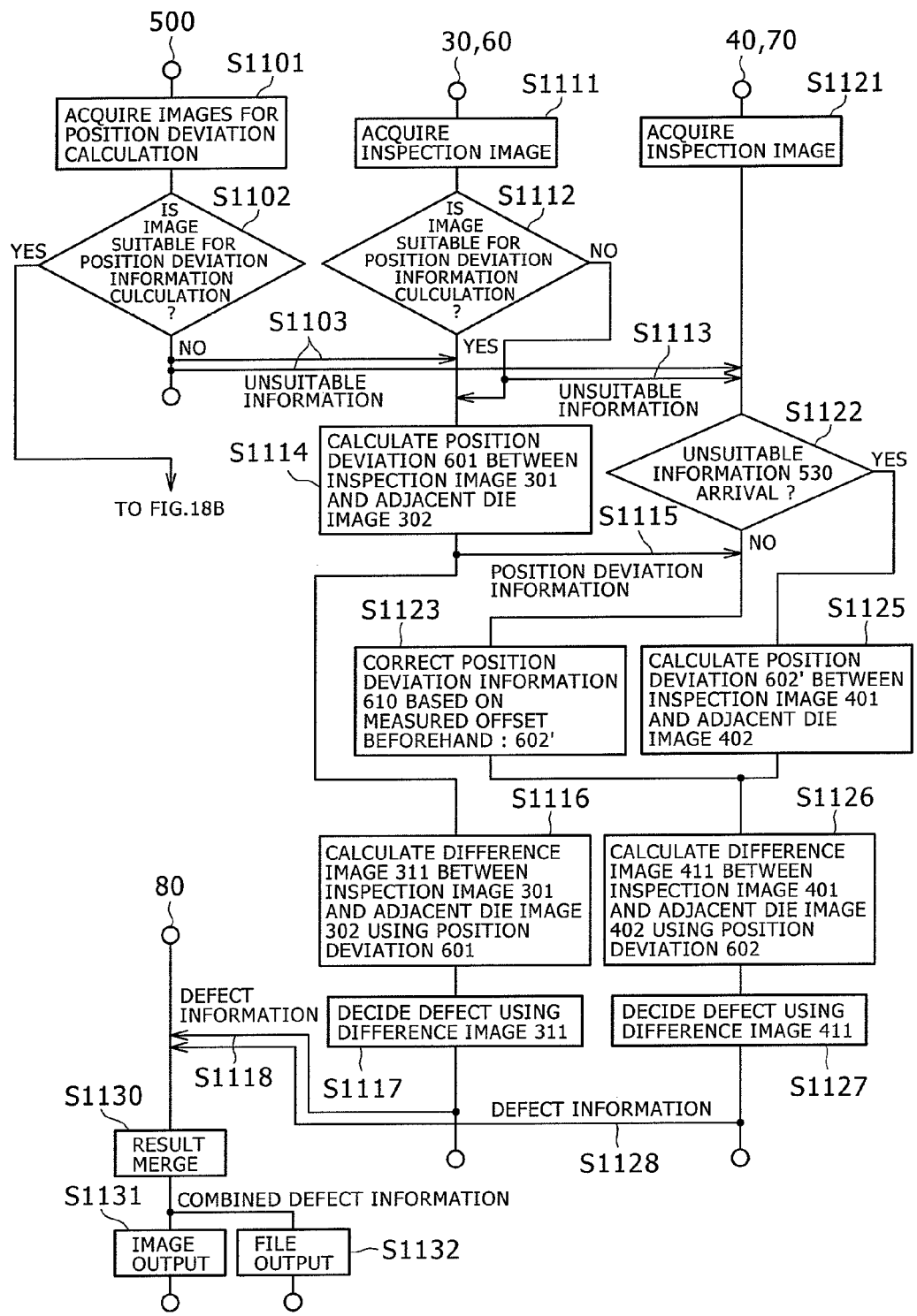
FIG. 18A is a flow diagram for the substrate inspection apparatus having two inspection heads and an image optical imaging system (bright field/white dark field) for merged deviation calculation in the case where the images obtained by the image optical imaging system for merged deviation calculation is suitable for calculating merged deviation information.
Figure 18B:
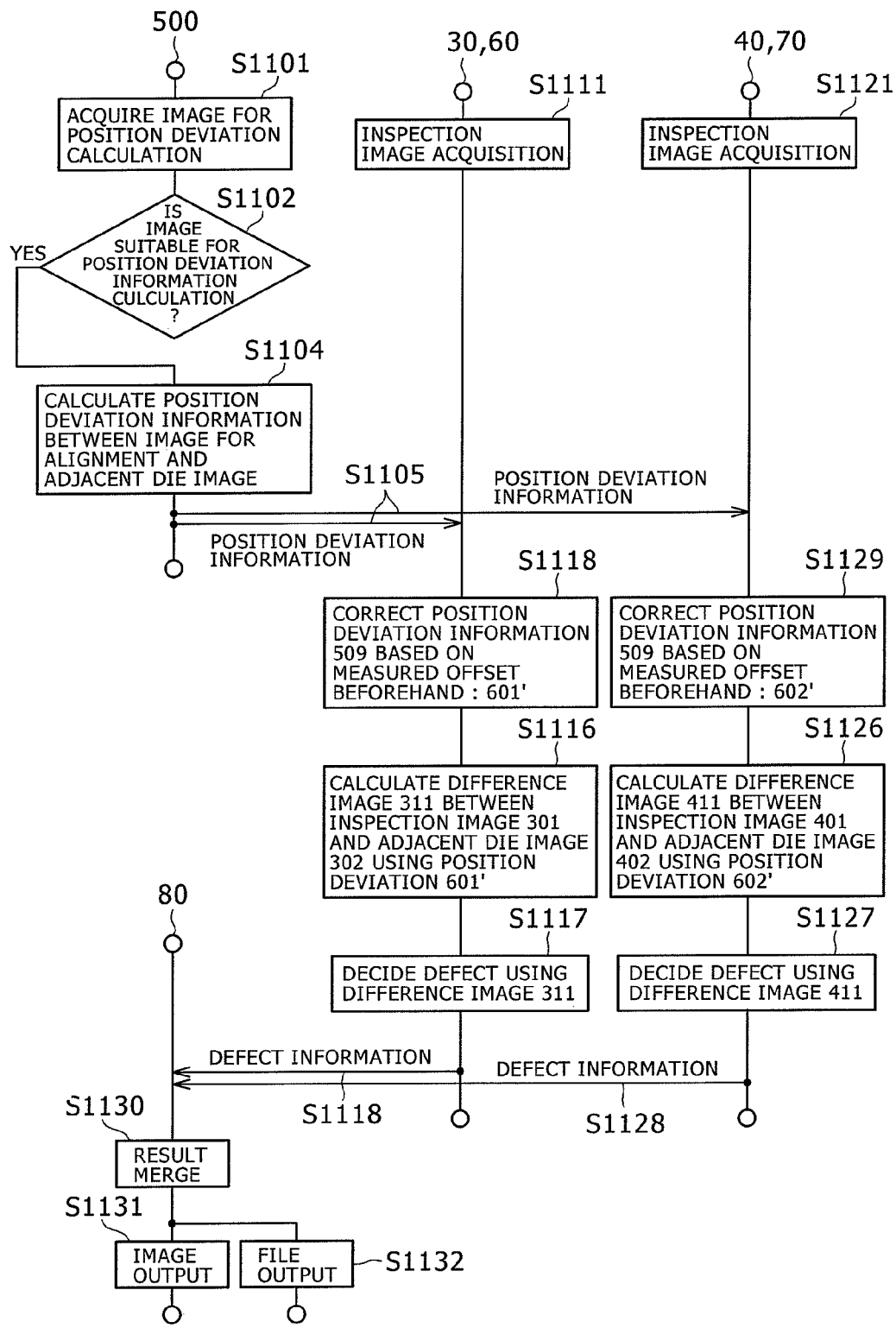
FIG. 18B is a flow diagram for the substrate inspection apparatus having two inspection heads and an image optical imaging system (bright field/white dark field) for merged deviation calculation in the case where the images obtained by the image optical imaging system for merged deviation calculation is not suitable for calculating merged deviation information.

Next, a second embodiment of this invention is described referring to FIGS. 17 and 18. FIG. 17 shows the block diagram of inspection apparatus 1. The Inspection apparatus 1 is constituted from the illuminating optical system 10, the substrate scanning system 20, and the first optical imaging system. The apparatus is further constituted from the second optical imaging system 40, the focus measurement system 50, a misalignment measurement system 500, the first image processing system 60, the second image processing system 70, the control processing system 80, and the interface system 90. Illuminating optical system 10 includes the laser light source 11 and the lens 12 for shaping the beam. The light emitted from the laser light source 11 is suitably shaped with the lens 12 and illuminates an inspection substrate 100. The substrate scanning system 20 includes the X stage 21, the Y stage 22, the Z stage 23, the substrate chuck 24, and the θ stage 25.

The first optical imaging system 30 includes the object lens 31, the spatial filter 32, the image formation lens 33, the polarizing filter 34, the photosensor 35, and the A/D-conversion unit 36. The second optical imaging system 40 includes the object lens 41, the spatial filter 42, the image formation lens 43, the polarizing filter 44, the photosensor 45, and the A/D-conversion unit 46. The focus measurement system 50 includes illuminating optical system 51, the optical imaging system 52, the photosensor 53, and the focus deviation calculation processing unit 54. The first image processing system 60 includes the image misalignment information calculation unit 61 between adjacent dies, and the data processing unit 62 for performing defect determination and detection processing using the difference image between dies. The second image processing system 70 includes the integrate image misalignment correction unit 71, and the data processing unit 72 for performing defect determination and detection processing using the difference image between dies. Misalignment measurement system 500 includes an illuminating optical system 510, a optical imaging system 520, a photosensor 503, and a misalignment calculation unit 504. The first image processing system 60 includes image misalignment information calculation unit 61 between contiguity dies, and data processing unit 62 for performing defect determination and detection processing using the difference image between dies. The second image processing system 70 includes the misalignment information correction unit 71 for correcting the integrated image misalignment information mentioned above, and the data processing unit 72 for performing defect determination and detection processing using the difference image between dies.

The control and processing unit 80 includes the transfer system control unit 81 for controlling at least the transfer system 20, the illumination light source control unit 82, and the sensor control unit 83 for acquiring a image in synchronization with the first optical imaging system 30 and second optical imaging system 40, The defect information processing unit 84 for performing merging and sorting processing of the defect information 600 outputted from the first image processing system 60, and the second image processing system 70, and the control unit 89 for controlling the whole.

The interface system 90 includes data accumulation section 91 for accumulating at least the defect information 650 processed and outputted by the control and processing unit 80, input section 92 for performing an inspection condition setup and an information inputting between control processing, and display section 93 for displaying defect information 650 or displays control management information.

Referring to FIGS. 18 and 28 the flow of operation is shown, among those related to the inspection of the second embodiment of the present invention, of the first optical imaging system 30 with the first image processing system 60, the second optical imaging system 40 with the second image processing system 70, the misalignment measurement system 500, and the control processing system 80. The semiconductor substrate 100 fixed to the wafer chuck 34 in the substrate scanning system 30 is scanned by the X direction stage 31, and synchronizing with this, surface images 301, 401, and 501 of the substrate 100 are acquired by the first optical imaging system 30, the second optical imaging system 40, and misalignment measurement system 500, respectively. The optical resolution of the first optical imaging system 30 is assumed to be equal to or higher than the second optical imaging system 40 optical resolution.

The operation flow of misalignment system of measurement 500 is explained first. The diffracted light and scattered light are produced with the surface of substrate 100 by illuminating the substrate 100 with the illumination light emitted from the illumination light source 507 and led to a photosensor 550 by an object lens 502 and focused to produce a surface image 519 through a photoelectric conversion and an A/D conversion in the misalignment measurement system 500 (S1101). The surface image 519 is sent to the misalignment information calculation unit 504 between adjacent dies. In the calculation unit 504, the information whether the surface image 519 is suitable for alignment is obtain (S1102). Other methods may be used although it is simple to determine whether the image of surface 519 has enough pattern part required for the position merge by calculating the contrast of the image. When it is decided that it is unsuitable, unsuitable information 520 is transmitted to misalignment information calculation unit 61 in the first image processing system 60, and correction unit 71 in the second image processing system 70. When decided as suitable, the misalignment information 509 between adjacent dies is computed, and the misalignment information 509 is transmitted to the correction unit 61 in the first image processing system 60, and the correction unit 71 in the second image processing system 70.

The above is an operation flow of misalignment measurement system 500.

Next, the flow of operation is described of the first optical imaging system 30 and the first image processing system 60'. The diffracted light and scattered light produced on the surface of the substrate 100 are converted to the current by the photoelectric conversion and A/D conversion in the photosensor 35 in the first optical imaging system 30, and produce a surface image 301 (S1111). The surface image 301 is sent to a misalignment information calculation unit 61' between adjacent dies. The information whether surface image 301 is suitable for position merging in the calculation unit 61' is acquired (S1112). Other methods may be used although it is simple to determine whether the image of surface 501 has enough pattern part required for the position merge by calculating the contrast of the image. When it is decided that it is unsuitable, unsuitable information 530 is transmitted to the correction unit 71 in the second image processing system 70. Next, the unsuitable information 520 or misalignment information 509 is received from the misalignment information calculation unit 504 between adjacent dies. Operations differ depending on which is received. The operation flow is explained first about the case where the unsuitable information 520 is received. In this case, the operation is almost the same as the operation of the first image processing system 60 in the first embodiment. With the misalignment information calculation unit 61' between adjacent dies of the first image processing system 60' the misalignment information 601 on the surface image 301 and adjacent die image 302 is computed (S1114), and transmitted to the misalignment information correction unit 71' of the second image processing system 70 as the misalignment information 610 together with the center coordinates 308 of the image (S1115). In the data processing unit 62 of the first image processing system 60', the difference image 311 between dies is calculated based on the misalignment information 610 between the adjacent dies computed by the surface image 301 and the misalignment information calculation unit 61' (S1116), and the defect determination and detection processing are performed using the computed difference image 311 (S1117). The obtained processing result is transmitted to the control processing system 80 as the defect information 611 (S1118). Although the defect information 611 includes at least the defect coordinate 312, it is preferable also to make the defect feature 313, the defect image 311, and the inspection image 301 into the defect information 611 collectively. The flow of operation is described above of the first image processing system 60 in the first optical imaging system 30 for the case where the unsuitable information 520 is received from the misalignment information calculation unit 504 between adjacent. Next, the flow of operation is described for the case where the misalignment information 509 is received from the misalignment information calculation unit 504 between adjacent dies. In this case, the operation is almost the same as the operation of the second image processing system 70 in the first embodiment. The misalignment information correction unit 61' corrects the misalignment information 509 transmitted from the misalignment information calculation unit 504 between adjacent dies in the deviation measurement system 500 based on the calibration information obtained beforehand (S1118), and transmits the misalignment information 601' after correction to the image processing unit 62. The image processing unit 62' calculates the difference image 311 between dies based on the surface image 301 outputted from the first optical imaging system 30 and the misalignment information 601' corrected by and misalignment information calculation unit 61' (S1116), and performs defect determination and detection processing using the difference image 311 (S1117). The obtained processing result is transmitted to the control processing system 80 as the defect information 611 (S1118). Although the defect information 611 includes at least the defect coordinate 312, it is preferable also to make the defect feature 313, the defect image 311, and the inspection image 401 into the defect information 611 collectively. The above is the flow of operation of the first optical imaging system 30 and the first image processing system 60'.

Next, the flow of operation is described of the second optical imaging system 40 and the first image processing system 70'. The diffracted light and scattered light produced on the surface of the substrate 100 are converted to the current by the photoelectric conversion and A/D conversion in the photosensor 45 in the second optical imaging system 40, and produce a surface image 401 (S1121). The surface image 401 is sent to a misalignment information calculation unit 71' between adjacent dies'. Next, the unsuitable information 520 or misalignment information 509 is received from the misalignment information calculation unit 504 between adjacent dies. In the case where unsuitable information 520 is received, the misalignment information 610 or the unsuitable information 530 from the data processing unit 61 of first image processing system 60'. The operation of the second image processing system 70' depends on which of the case. The flow of operation is described for the case where the unsuitable information 520 and the unsuitable information 530 are received. In this case, the operation is almost the same as the operation of the first image processing system 60 in the first embodiment. With the misalignment information calculation unit 71' between adjacent dies of the first image processing system 70' the misalignment information 602' on the surface image 401 and adjacent die image 402 is computed (S1125), based on the misalignment information 602' the difference image 311 is calculated (S1126), and the defect determination and detection processing are performed using the computed difference image 411 (S1127). The obtained processing result is transmitted to the control processing system 80 as the defect information 612 (S1128). Although the defect information 612 includes at least the defect coordinate 412, it is preferable also to make the defect feature 413, the defect image 411, and the inspection image 401 into the defect information 612 collectively. The flow of operation is described above of the second optical imaging system 40 and the second image processing system 70' for the case where the unsuitable information 520 is received from the misalignment information calculation unit 504 between adjacent dies and the unsuitable information 530 is received from the misalignment information calculation unit 61' between adjacent dies, respectively.

Next, the flow of operation is described for the case where the misalignment information 509 is received from the misalignment information calculation unit 504 between adjacent dies. In this case, the operation is almost the same as the operation of the first image processing system 60' in the first embodiment, in which the misalignment information 509 is received from the misalignment information calculation unit 504 between adjacent dies. The misalignment information correction unit 71' corrects the misalignment information 509 transmitted from the misalignment information calculation unit 504 between adjacent dies in the deviation measurement system 500 based on the calibration information obtained beforehand (S1129), and transmits the misalignment information 602' after correction to the image processing unit 72'. The image processing unit 72' calculates the difference image 411 between dies based on the surface image 401 outputted from the second optical imaging system 40, the adjacent image 402, and the misalignment information 602' corrected by and misalignment information calculation unit 71' (S1126), and performs defect determination and detection processing using the difference image 411 (S1127). The obtained processing result is transmitted to the control processing system 80 as the defect information 612 (S1128). Although the defect information 612 includes at least the defect coordinate 412, it is preferable also to make the defect feature 413, the defect image 411, and the inspection image 401 into the defect information 611 collectively. The above is the flow of operation of the second optical imaging system 40 and the second image processing system 70'. The flow of operation is described above of the second optical imaging system 40 and the second image processing system 70' for the case where the misalignment information 509 is received from the misalignment information calculation unit 504 between adjacent dies.

Finally, the flow of operation is described for the case where the unsuitable information 520 and the misalignment information 610 are received from the misalignment information calculation unit 504 between adjacent dies and the data processing unit 61' of the first image processing system 60', respectively. In this case, the operation flow is nearly the same as that of the second image processing unit 70 in the first embodiment. The misalignment information correction unit 71' corrects the misalignment information 509 received from the data processing unit 61' of the first image processing system 60' based on the calibration information obtained beforehand (S1129), and transmits the misalignment information 602' after correction to the image processing unit 72'. The image processing unit 72' calculates the difference image 411 between dies based on the surface image 301 outputted from the first optical imaging system 30 and the misalignment information 602' corrected by and misalignment information calculation unit 71' (S1126), and performs defect determination and detection processing using the difference image 411 (S1127). The obtained processing result is transmitted to the control processing system 80 as the defect information 612 (S1128). Although the defect information 612 includes at least the defect coordinate 412, it is preferable also to make the defect feature 413, the defect image 411, and the inspection image 401 into the defect information 612 collectively. The above is the flow of operation of the second optical imaging system 40 and the second image processing system 70'. The flow of operation is described above of the second optical imaging system 40 and the second image processing system 70' for the case where the unsuitable information 520 is received from the misalignment information calculation unit 504 between adjacent dies and the misalignment information 610 is received from the data processing unit 61' of the first data processing system 60', respectively.

Next, the operation flow of control processing system 80 is explained. Using the coordinates 312 and 412 of each defect transmitted from the first image processing system 60' and the second image processing system 70', defect information 611612 is decided to be the same defect and merged, and integrated defect information 619 is generated (S1131). The integrated defect information 619 is outputted as file information through input output means 92 and accumulation means 91 (S1132), or displayed on the screen of 93 (S1133). Although an example is shown of an inspection apparatus having the optical system for combining deviation calculation, and a plurality of optical imaging systems, also in the present embodiment as in the first embodiment explained, by obtaining the offset value between the optical systems and optical imaging systems for combining deviation calculation beforehand, it becomes possible to merge the defect information on the substrate detected by each optical imaging system, and to defect with higher sensitivity using more information. By providing an optical system for combined deviation calculation with resolving power higher than that of a defect inspection optical system, an improvement in calculating the combined deviation accuracy is achieved and it becomes possible to defect with higher sensitivity.

Eighth Embodiment

Figure 20:
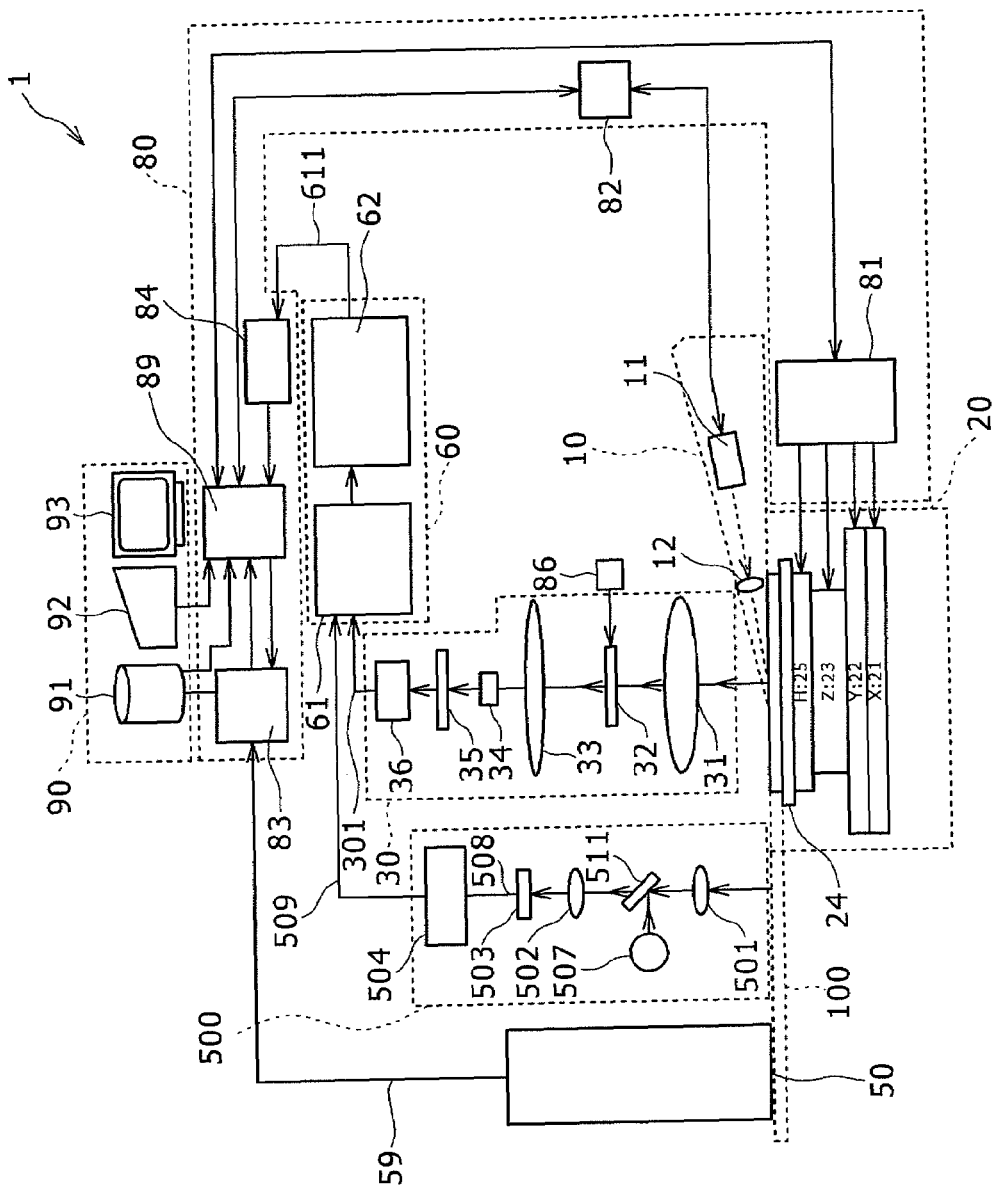
FIG. 20 shows a configuration of the substrate inspection apparatus having one inspection head and an image optical imaging system (bright field/white dark field) for merged deviation calculation.
Figure 21:
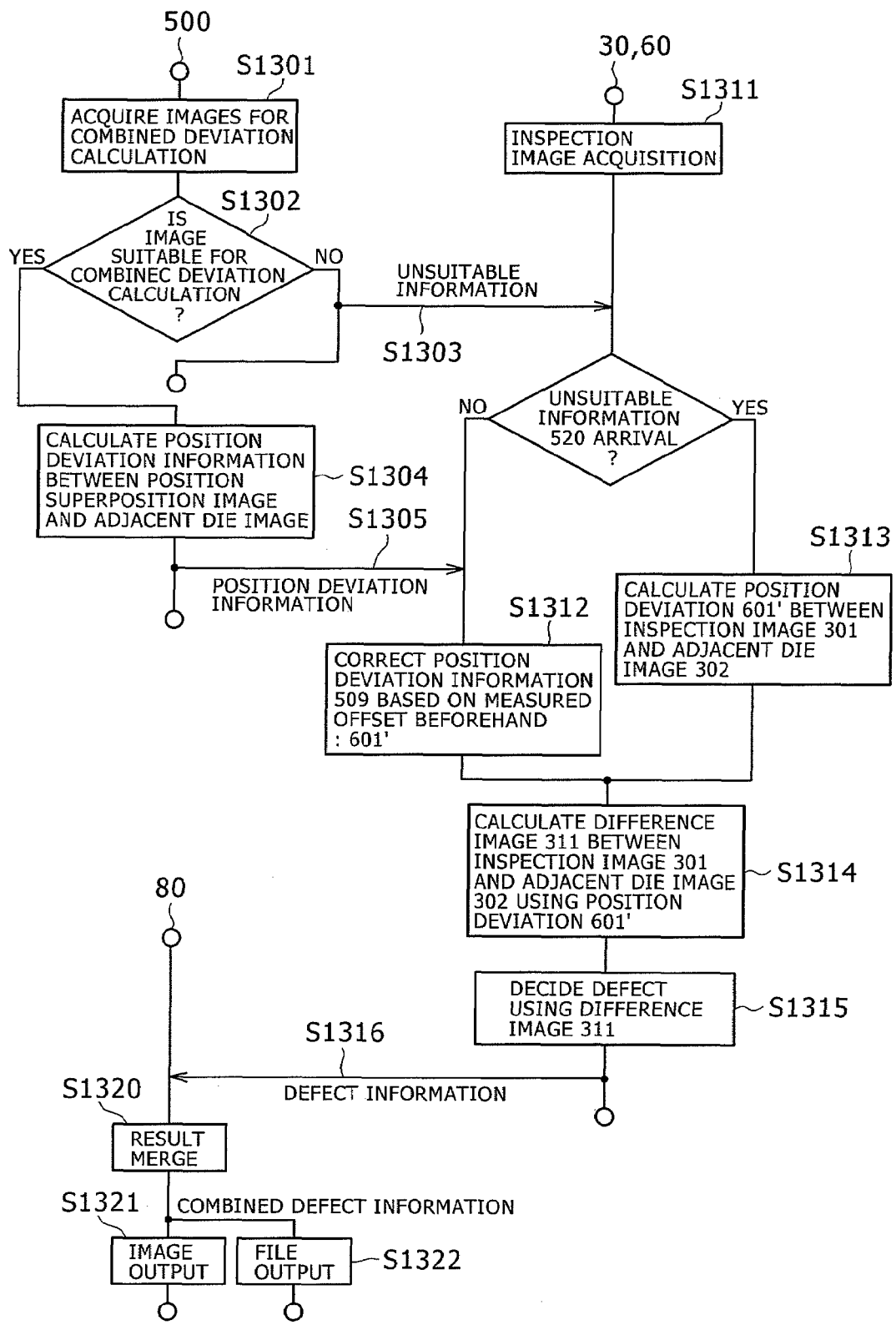
FIG. 21 is a flow diagram for the substrate inspection apparatus having one inspection head and an image optical imaging system (bright field/white dark field) for merged deviation calculation.

Next, a third embodiment of this invention with the constitution of defect inspection system having the combined deviation measurement is shown in FIG. 20 together with the operation flow in FIG. 21. The block diagram of the inspection apparatus 1 is shown in FIG. 20. The inspection apparatus 1 comprises an illuminating optical system 10, a substrate scanning system 20, a optical imaging system 30, a focus measurement system 50, misalignment measurement system 500, an image processing system 60', control processing system 80 and an interface system 90. The illuminating optical system 10 is provided with a laser light source 11, a lens 12 for beam shaping, and performs suitably beam shaping for the light emitted from the laser light source 11 with the lens 12, and illuminates a inspected substrate 100. The substrate scanning system 20 is provided with an X stage 21, a Y stage 22, a Z stage 23, a substrate chuck 24, and a ● stage 25. The optical imaging system 30 is provided with an object lens 31, a spatial filter 32, an image formation lens 33, a polarizing filter 34, a photosensor 35, and an A/D-conversion unit 36.

The focus measurement system 50 includes an illumination system 51, a optical imaging system 52, a photosensor 53, and a focus deviation calculation processing unit 54. The image processing system 60' includes a misalignment information calculation unit 61 between adjacent dies, and a data processing unit 62' performing a defect identification and detection processing using a difference image between dies. Misalignment measurement system 500 includes an illuminating optical system 510, a optical imaging system 520, a photosensor 503, and a misalignment information calculation unit 504. The control and processing system 80 includes at least a transfer system control unit 81, an illumination light source control unit 82, a sensor control unit 83 for acquiring an image, synchronizing the first optical imaging system 30 with the second optical imaging system 40, a defect information processing unit 84 for performing merging and sorting process of the defect information 600 outputted from the first image processing system 60, and the second image processing system 70, and the control unit 89 for controlling the whole. The interface system 90 includes a data accumulation section 91 for accumulating defect information 650 processed and outputted by the control and processing system 80, an input section 92 for performing verification condition setup and control processing information input, and a display section 93 for displaying defect information 650 or control processing information.

The operation flow of the optical imaging system 30, the image processing system 60, the combining deviation measurement system 500, and the control processing system 80 is shown in FIG. 21. The operation flow of misalignment measurement system 500 is explained first. This is almost the same as that of the operation flow of the misalignment measurement system 500 in the 2nd embodiment of this invention. By illuminating the substrate 100 with the light from the illumination light source 507, the scattered light and diffracted light are produced through object lens 502 and led to the photo sensor 550. The surface image 519 is obtained through photoelectric conversion and A/D conversion by the photosensor 550 in the misalignment measurement system (S1301). The surface image 519 is sent to the misalignment information calculation unit 504 between adjacent dies. In calculation unit 504, the information whether surface image 519 is suitable for position alignment is acquired (S1302).

Other methods may be used although it is simple to determine whether the method of misalignment information decision computes the contrast of the picture of surface image 519, and decide pattern parts required for alignment is enough. When it is decided that it is unsuitable, unsuitable information 520 is transmitted to the misalignment information calculation unit 61' in the image processing system 60. When decided as suitable, the misalignment information 509 between adjacent dies is computed, and the misalignment information 509 is transmitted to the correction unit 61 in the 1st image processing system 60, and the correction unit 71 in the 2nd image processing system 70. The above is an operation flow of the misalignment measurement system 500.

Next, the flow of operation is described of the optical imaging system 30 and the first image processing system 60'. The diffracted light and scattered light produced on the surface of the substrate 100 are converted to the current by the photoelectric conversion and A/D conversion in the photosensor 35 in the optical imaging system 30, and produce a surface image 301 (S1311). The surface image 301 is sent to a misalignment information calculation unit 61' between adjacent dies'. the unsuitable information 520 or misalignment information 509 is received from the misalignment information calculation unit 504 between adjacent dies. Operations differ depending on which is received. In the case where the unsuitable information 520 is received the misalignment information calculation unit 61' between adjacent dies of the image processing system 60' calculate the misalignment information 601' on the surface image 301 and adjacent die image 302 (S1114), and sends to the image processing unit 72' In the case where misalignment information 509 is received, the misalignment information 509 is corrected based on the calibration information searched for beforehand (S1312), and the misalignment information 601' after correction is sent to the image processing unit 72'. The data processing unit 62' of the image processing system 60' calculates the difference image 311 between dies based on the surface image 301 and the misalignment information 601' obtained by the misalignment information calculation unit 61' (S1314), and performs defect determination and detection processing using this computed difference image 311 (S1315). The obtained processing result is transmitted to the control processing system 80 as the defect information 611 (S1316). Although the defect information 611 includes at least the defect coordinate 312, it is preferable also to make the defect feature 313, the defect image 311, and the inspection image 301 into the defect information 611 collectively. The above is the flow of operation of the optical imaging system 30 and the image processing system 60.

Next, the operation flow of control processing system 80 is explained. Using coordinates 312 of each defect, the same defect is decided and the defect information 611 transmitted from the image processing system 60' is merged (S1320). The merged defect information is outputted as file information through the input output means 92 and the accumulation means 91 (S1321), or an image on the screen of display 93 (S1322).

In this embodiment, although the example of an inspection apparatus is shown provided with the optical system for combining deviation calculation, and the optical imaging system, it becomes possible to defect with higher sensitivity b By providing an optical system for combined deviation calculation with resolving power higher than that of a defect inspection optical system, an improvement in calculating the combined deviation accuracy is achieved and it becomes possible to defect with higher sensitivity. It became possible to raise the calculation accuracy of a doubling gap, and it became possible to defect by higher sensitivity.

The invention may be embodied in other specific forms without departing from the spirit or essential characteristics thereof. The present embodiment is therefore to be considered in all aspects as illustrative and not restrictive, the scope of the invention being indicated by the appended claims rather than by the foregoing description and all changes which come within the meaning and range of equivalency of the claims are therefore intended to be embraced therein.

What is claimed is:

1. A defect inspection method for a semiconductor substrate comprising the following steps of:
   irradiating a surface of an inspected object with light emitted from an illumination light source;
   detecting light radiated from the inspected object via a first optical imaging system that has a first optical resolution and at least a second optical imaging system which has an optical resolution lower than the first optical resolution, and imaging a plurality of surface images of the inspected object to be detected;
   calculating an amount of a first misalignment between an inspection image chosen from the surface images acquired by the first optical imaging system and a reference image chosen from the several surface images different from the inspection image;
   deciding and detecting a defect based on the reference image and the inspection image corrected in accordance with the calculated amount of the first misalignment by use of the first optical imaging system;
   storing a first defect information including defect coordinates detected by the first defect detecting step;
   setting parameters required for calibration to correct a second amount of misalignment produced from the surface images imaged by the first optical imaging system and the second optical imaging system;
   correcting the inspection image using the second amount of misalignment corrected based on the calibration;
   deciding and detecting a second defect based on the corrected inspection image and the reference image; and
   storing a second defect information including defect coordinates detected by the second defect.

2. The defect inspection method for a semiconductor substrate according to claim 1, further comprising the step of merging the first and the second defect information based on the defect coordinates.

3. The defect inspection method for a semiconductor substrate according to claim 1, wherein the parameters required for the calibration is set using the semiconductor substrate the surface coordinates thereof is known.

4. The defect inspection method for a semiconductor substrate according to claim 1, wherein a plurality of optical imaging systems including the first optical imaging system and the second optical imaging system are fixed to the same block in which each original vibration is suppressed.

5. The defect inspection method for a semiconductor substrate according to claim 1, further comprising a step of:
   distinguishing whether the defect information of the first and the second defect information is a misreport or not based on the defect coordinate; and
   outputting the defect information decided as a misreport from defect information not distinguished as a misreport.

6. The defect inspection method for a semiconductor substrate according to claim 1, further comprising the steps of:
   measuring a defocus distance of an optical system against the substrate surface to be inspected, an optical axis direction of said optical system is different from a direction perpendicular to the substrate surface;

calculating a third amount of misalignment in addition to the amount of misalignment calibrated from the second amount of misalignment from the measured amount of defocusing; and correcting the inspection image using the third amount of misalignment.

7. The defect inspection method for a semiconductor substrate according to claim 1, further comprising the steps of:

illuminating a different region from the region on the surface of the inspected object where the illumination light source illuminates, with light emitted from a different light source from the illumination light source;

obtaining the surface image of the different region illuminated by the different light source, calculating the fourth amount of misalignment of the inspection image and the reference image based on the surface image of the different region, and calibrating the fourth amount of misalignment as the first amount of misalignment.

8. The defect inspection method for a semiconductor substrate according to claim 1, wherein the step of deciding and detecting a defect based on the reference image and the inspection image corrected includes calculating a difference image between the reference image and the inspection image corrected and deciding and detecting the defect based on the difference image, and wherein the step of deciding and detecting a second defect based on the corrected inspection image and the reference image includes deciding an detecting the second defect based on the difference image calculated from the difference between the corrected inspection image and the reference image.

9. A defect inspection apparatus of a semiconductor substrate, comprising:

an illumination light source for emitting light to a surface of a semiconductor substrate of the inspected object;

the first optical imaging system having a first optical resolution that images the image by the radiated light from the surface of the irradiated semiconductor substrate;

the second optical imaging system that has an optical resolving power lower than the first optical resolution, and images the image by the radiated light from the surface of the semiconductor substrate of the inspected subject to be irradiated;

means for calculating a first amount of misalignment between the images of a inspection image chosen from a plurality of the surface images of the semiconductor substrate imaged by the first optical imaging system and a reference image chosen from the several surface images different from the detected image;

first defect detection means for correcting the amount of misalignment of the inspection image and the reference image using the information on the first amount of misalignment calculated and deciding and detecting the defect based on the reference image and the inspection image corrected in accordance with the calculated first amount of misalignment;

means for storing the first defect information including the position coordinates of the defect detected by the first defect detection means;

means for calculating parameters required for the calibration for correcting the second amount of misalignment produced between the surface image of the semiconductor substrate imaged by the first optical imaging system and the surface image of the semiconductor substrate imaging by the second optical imaging system;

means for correcting the inspection image using the second amount of misalignment corrected by calibration using the calculated parameters by means for calculating parameter;

second defect detection means for deciding and detecting the defect based on the corrected inspection image and the reference image;

means for storing the second defect information including the defect coordinates detected by the second defect detection means; and means for merging the first and second defect information based on the defect coordinates.

10. The defect inspection apparatus for a semiconductor substrate according to claim 9, wherein a plurality of optical imaging systems including the first optical imaging system and the second optical imaging system are fixed to the same block in which each original vibration is suppressed.

11. The defect inspection apparatus for a semiconductor substrate according to claim 9, further comprising means for distinguishing whether the defect information of the first and the second defect information is a misreport or not based on the defect coordinate, means for distinguishing outputting the defect information distinguished as a misreport from defect information not distinguished as a misreport.

12. The defect inspection apparatus for a semiconductor substrate according to claim 9, further comprising means for measuring a defocus distance of an optical system with the image detecting surface which is not parallel to the substrate surface of the inspected object, wherein the means for correcting the inspection image obtains a third amount of misalignment in addition to the amount of misalignment calibrated second amount of misalignment from the defocus distance measured by means for measuring the defocus distance, and correct the inspection image using the third amount of misalignment.

13. The defect inspection apparatus for a semiconductor substrate according to claim 9, further comprising:

a different light source from the illumination light source which illuminates a different region from the region on the surface of the inspected object illuminated by the illumination light source;

means for obtaining the surface image of the different regions illuminated by the different light sources, and calculating a fourth amount of misalignment between the inspection image and the reference image based on the surface image of the acquired different regions;

means for calibrating the fourth amount of misalignment as the first amount of misalignment.

14. The defect inspection apparatus for a semiconductor substrate according to claim 9, wherein the first defect detection means includes means for calculating a difference image from the reference image and the inspection image corrected, and the second defect detection means decides and detects the defect based on the difference image calculated from the corrected inspection image and the reference image.

* * * * *